United States Patent
Alqahtani et al.

(10) Patent No.: US 11,951,191 B2
(45) Date of Patent: Apr. 9, 2024

(54) DENTAL MATERIAL CONTAINING NANOSIZED FILLERS AND PREPARATION METHODS THEREOF

(71) Applicant: University of Tabuk, Tabuk (SA)

(72) Inventors: Mana Alqahtani, Tabuk (SA); Nacer Badi, Tabuk (SA)

(73) Assignee: University of Tabuk, Tabuk (SA)

( * ) Notice: Subject to any disclaimer, the term of this patent is extended or adjusted under 35 U.S.C. 154(b) by 315 days.

(21) Appl. No.: 17/122,698

(22) Filed: Dec. 15, 2020

(65) Prior Publication Data

US 2021/0186822 A1 Jun. 24, 2021

Related U.S. Application Data

(60) Provisional application No. 62/951,112, filed on Dec. 20, 2019.

(51) Int. Cl.
| | |
|---|---|
| *A61K 6/818* | (2020.01) |
| *A61C 5/77* | (2017.01) |
| *A61C 13/00* | (2006.01) |
| *A61C 13/20* | (2006.01) |
| *A61K 6/17* | (2020.01) |
| *A61K 6/60* | (2020.01) |
| *A61K 6/802* | (2020.01) |
| *A61K 6/889* | (2020.01) |
| *B29B 7/90* | (2006.01) |

(Continued)

(52) U.S. Cl.
CPC ................ *A61K 6/818* (2020.01); *A61C 5/77* (2017.02); *A61C 13/0016* (2013.01); *A61C 13/20* (2013.01); *A61K 6/17* (2020.01); *A61K 6/60* (2020.01); *A61K 6/802* (2020.01); *A61K 6/889* (2020.01); *B29B 7/90* (2013.01); *B29C 43/003* (2013.01); *B29C 43/32* (2013.01); *B29K 2033/12* (2013.01); *B29K 2509/02* (2013.01); *B29L 2031/7532* (2013.01)

(58) Field of Classification Search
CPC ....................................................... A61C 5/77
See application file for complete search history.

(56) References Cited

U.S. PATENT DOCUMENTS

| | | | |
|---|---|---|---|
| 5,936,006 A | 8/1999 | Rheinberger et al. | |
| 7,649,029 B2 | 1/2010 | Kolb et al. | |

(Continued)

FOREIGN PATENT DOCUMENTS

| | | | | |
|---|---|---|---|---|
| EP | 2712656 A2 * | 4/2014 | ........... | A61K 8/0245 |
| EP | 2712656 A2 | 4/2014 | | |
| WO | WO-2020262814 A1 * | 12/2020 | ......... | A61C 13/0022 |

OTHER PUBLICATIONS

Yang et al. "Hexagonal Boron Nitride UDMA Resin Composites", IADR: 96th General Session & Exhibition of the IADR, 2018. (Year: 2018).*

(Continued)

*Primary Examiner* — Ryan M Ochylski
*Assistant Examiner* — Ariella Machness
(74) *Attorney, Agent, or Firm* — Justin R. Muehlmeyer; Peacock Law P.C.

(57) ABSTRACT

A filled self-cured dental material is described comprising inorganic boron nitride and/or zirconia particles in a solvent dispersion agent, the nanoparticles being entrained by an ultrasonic homogenizer technique to enhance both strength and stiffness of the dental material.

20 Claims, 18 Drawing Sheets

(51) Int. Cl.
  *B29C 43/00* (2006.01)
  *B29C 43/32* (2006.01)
  *B29K 33/00* (2006.01)
  *B29K 509/02* (2006.01)
  *B29L 31/00* (2006.01)

(56) References Cited

U.S. PATENT DOCUMENTS

| 7,892,342 | B2 | 2/2011 | Primus |
| 2015/0196462 | A1 | 7/2015 | Sun |
| 2020/0253691 | A1* | 8/2020 | Utterodt .................. A61C 5/77 |

OTHER PUBLICATIONS

Franklin et al. "Reinforcement of poly(methyl methacrylate) denture base with glass flake" Dental Materials (2005) 21, 365-370. (Year: 2005).*

Paidi et al. "Comparative Study of Flexural Strength and Fracture Resistance of Two Different Types of Provisional Restorative Materials Reinforced with Two Different Fibers—An In-Vitro Study" International Journal of Current Research (2017) 9, 6, 52688-52694 (Year: 2017).*

Gautam et al. "3D interconnected architecture of h-BN reinforced ZrO2 composites: Structural evolution and enhanced mechanical properties for bone implant applications" Ceramics International (2019) 45, 1037-1048 (Year: 2019).*

GC Unifast III Instructions for Use (IFU), GC Dental Products Corp, Sep. 2008 (Year: 2008).*

GC Unifast III Powder Material Safety Data Sheet, GC Dental Products Corp, Oct. 2008 (Year: 2008).*

GC Unifast III Liquid Material Safety Data Sheet, GC Dental Products Corp, Jun. 2012 (Year: 2012).*

Collares et al. ("Boron Nitride Nanotubes as Filler for Resin-Based Dental Sealants" Scientific Reports, (2019) 9, 7710) (Year: 2019).*

Astudillo-Rubio, Daniela, et al., "Mechanical properties of provisional dental materials: A systemaric review and meta-analysis", PloS one 13.2, Feb. 28, 2018.

Bohns, Fabio Rocha, et al., "Boron Nitride Nanotubes as Filler for Resin-Based Dental Sealants", Scientific reports 9.1, May 22, 2019, 1-8.

Degrazia, Felipe Weidenbach, et al., "Boron nitride nanotubes as novel fillers for improving the properities of dental adhesives", Journal of dentistry 62, Jul. 1, 2017, 85-90.

Engler, Martin, et al., "Hexagonal Boron Nitride (hBN)—Applications from Metallurgy to Cosmetics", InCFI. Ceramic forum international 2007 (vol. 84, No. 12), 2007.

* cited by examiner

DENTAL MATERIAL CONTAINING NANOSIZED FILLERS AND PREPARATION METHODS THEREOF

CROSS-REFERENCE TO RELATED APPLICATIONS

This application claims priority to and the benefit of the filing of U.S. Provisional Patent Application No. 62/951,112, entitled "Dental Material Containing Nanosized Fillers and Preparation Methods Thereof", filed on Dec. 20, 2019, and the specification and claims thereof are incorporated herein by reference.

BACKGROUND OF THE INVENTION

Field of the Invention

Embodiments of the present invention relate to dental restorations and more specifically to self-cured dental materials containing nanosized inorganic fillers and to mixing techniques for production of composites with high mechanical strength and/or stiffness properties.

Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Provisional or temporary restorations such as inlays, crowns, bridges, and repairs are commonly used in dentistry prior to placing a final restoration. However, they are subjected to repeated chewing forces and require specific mechanical properties to be able to function in the oral environment. Polymethyl methacrylate (PMMA) is the preferred resin material in restorative dentistry because of its low water sorption and solubility, lack of toxicity, simple manipulation technique, excellent aesthetics and reparability. Non-modified PMMA behaves in a brittle manner when under load, especially under an impact force. Studies have focused on the development of curing methods, resin monomer development, and the pre-treatment of inorganic fillings to improve the properties of resin-based compounds. Heat treatment and post treatment increase the degree of polymerization and, to some extent, improve the strength of the composite. Reinforcing with carbon fibers, glass fibers, and metal powders are one of the modifications to produce an acrylic co-polymerized with relatively high impact strength. A systematic review and meta-analysis was carried out to examine the mechanical properties of provisional restoration materials used with direct techniques, as discussed in D. Astudillo-Rubio et al, "Mechanical properties of provisional dental materials: A systematic review and meta-analysis", PLOS ONE 13(2), 2018.

Efforts are directed toward the use of nano-sized fillers to reinforce the acrylic resins, therefore producing a polymer nanocomposite with improved mechanical and physical properties as compared to those filled with micro-scale particles. However, the mechanical mixing of constituents tends to be ineffective and often result in poor filler dispersion in the polymer matrix, especially when the filler size is in the sub-micrometer range. Furthermore, dental applications require high-quality materials that are biocompatible, wear-resistant, and durable. Boron nitride materials perfectly meet these conditions. The lubricating properties of fine-grained hexagonal boron nitride ("h-BN") are used in pencil leads, paints, cosmetics, and dental cements. Hexagonal boron nitride is currently used by nearly all leading producers of cosmetic products for foundations, make-up, eye shadows, blushers, kohl pencils, lipsticks and other skincare products, M. Engler, "Hexagonal Boron Nitride (hBN)—Applications from Metallurgy to Cosmetics" (2007) 84, p 12. In general, the hardness of h-BN is inferior only to diamond. Because of excellent thermal and chemical stability, h-BN is widely used in mechanical applications. The properties of the reinforced material depend on the size, shape, type, and concentration of the added particles to the host monomers. European Patent No. 2712656 A2 to Nuran et al. discloses the use of nano-size h-BN to prevent the formation of dental calculus. An article by F. Weidenbach Degrazia et al, Journal of Dentistry 62, 85 (2017) discloses the use of boron nitride nanotubes as novel fillers for improving the properties of dental adhesives. An article by Fabio Rocha Bohns et al, Scientific Reports (2019) reports on the use of boron nitride nanotubes as filler for resin-based dental sealants.

Hence, there is a need to provide a dental restoration material having high-strength and high-stiffness. It is also desirable that the material be biocompatible with optimum structural integrity and reliability.

BRIEF SUMMARY OF EMBODIMENTS OF THE PRESENT INVENTION

It is an object of embodiments of the present invention to make available a self-cured dental material which, compared with materials made by conventional mixing techniques, shows improved mechanical properties.

It is another object of embodiments of the present invention to make available a filled self-cured dental material which, compared with materials made by conventional mixing techniques, show improved mechanical properties.

It is yet another object of embodiments of the present invention to provide such dental material that contains boron nitride and/or zirconia nanoparticles.

Embodiments of the present inventions are directed to a dental material comprising: a resin; a solvent: and at least one filler, wherein the at least one filler comprises at least one selected from the group of: boron nitride and zirconia. In another embodiment, the boron nitride comprises boron nitride in hexagonal form (h-BN). In another embodiment, the boron nitride comprises a Wurtzite form, which is also hexagonal. In another embodiment, the boron nitride has an average particle size of about 10 nm to about 800 nm. In another embodiment, the dental material comprises a concentration of between about 0.25% and about 10% by weight of h-BN. In another embodiment, the zirconia has an average particle size of about 20 nm to about 800 nm. In another embodiment, the dental material comprises a concentration of between about 0.5% and about 20% by weight of Zirconia. In another embodiment, the resin is in powder form and the solvent is in liquid form and the ratio of resin to solvent is between about 2.0 gm of powder resin to about 1.0 ml of liquid solvent and about 2.0 gm of powder resin to about 2.0 ml of liquid solvent. In another embodiment, the resin is a self-curing acrylic resin comprising ethyl-methyl methacrylate polymer and polymethylmethacrylate. In another embodiment, the solvent is a liquid monomer comprising: methyl methacrylate; ethyleneglycol dimethacrylate; and trimethylolpropane trimethacrylate. In another embodiment, the dental material has a Vickers hardness of between about 1,019 MPa and 4,550 MPa. In another embodiment: the resin comprises a powder comprising greater than about 70% Ethyl-methyl methacrylate polymer and less than about 30% Polymethylmethacrylate; the solvent comprises a liquid comprising about 92.0% Methyl methacrylate, about 4.0% N,N-dimethyl-p-toluidine, about 2.0% Ethyleneglycol dimethacrylate and about 1.8% Trimethylolpropane trimethacrylate; the at least one filler comprises boron nitride and zirconia, wherein the boron nitride is in hexagonal form with particles having an average particle size of between about 10 nm and about 800 nm and making up between about 0.25% and about 10% by weight of the dental material, and wherein the zirconia has an average particle size of between about 20 nm and about 800 nm and making up between about 0.5% and about 20% by weight of the dental material.

Embodiments of the present invention are also directed to a method of preparing a dental material comprising mixing at least one filler with a solvent and a resin to create a composite, wherein the at least one filler comprises at least one selected from the group of: boron nitride and zirconia. In another embodiment, the method includes pouring the composite into a mold.

In another embodiment, the mold comprises an opening to release extra composite, and further comprises pressing the mold with the composite therein by compression. In another embodiment, the method includes pressing the mold with the composite therein by compression and setting the molds with the compressed composite therein to form the dental material. In another embodiment, the method includes milling the dental material to form a dental restoration. In another embodiment, the solvent is in liquid form and the resin is in powder form, and further comprises: mixing the at least one filler with the liquid solvent before mixing with the powder resin, to create a solvent-filler mixture; and mixing the solvent-filler mixture with the powder resin to create the composite. In another embodiment, the step of mixing the at least one filler with the liquid solvent comprises using ultrasonic mixing. In another embodiment, the boron nitride comprises boron nitride in hexagonal form (h-BN). In another embodiment, the dental material comprises a concentration of between about 0.25% and 10% by weight of h-BN. In another embodiment, the boron nitride has an average particle size of about 10 nm to about 800 nm. In another embodiment, the dental material comprises a concentration of between about 0.5% and about 20% by weight of Zirconia. In another embodiment, the zirconia has an average particle size of about 20 nm to about 800 nm. In another embodiment, the resin is in powder form and the solvent is in liquid form and the ratio of resin to solvent is between about 2.0 gm of powder resin to about 1.0 ml of liquid solvent and about 2.0 gm of powder resin to about 2.0 ml of liquid solvent. In another embodiment, the resin is a self-curing acrylic resin comprising ethyl-methyl methacrylate polymer and polymethylmethacrylate. In another embodiment, the solvent is a liquid monomer comprising: methyl methacrylate; ethyleneglycol dimethacrylate; and trimethylolpropane trimethacrylate. In another embodiment: the resin comprises a dental powder comprising greater than about 70% Ethyl-methyl methacrylate polymer and less than about 30% Polymethylmethacrylate; the solvent comprises a liquid comprising about 92.0% Methyl methacrylate, about 4.0% N,N-dimethyl-p-toluidine, about 2.0% Ethyleneglycol dimethacrylate and about 1.8% Trimethylolpropane trimethacrylate, wherein the ratio of resin to solvent is between about 2.0 gm of powder resin to about 1.0 ml of liquid solvent and about 2.0 gm of powder resin to about 2.0 ml of liquid solvent; and the at least one filler comprises boron nitride and zirconia, wherein the boron nitride is in hexagonal form with particles having an average particle size of between about 10 nm and about 800 nm and making up between about 0.25% and about 10% by weight of the dental material, and wherein the zirconia has an average particle size of between about 20 nm and about 800 nm and making up between about 0.5% and about 20% by weight of the dental material; and further comprises: mixing the at least one filler with the liquid solvent before mixing with the powder resin, to create a solvent-filler mixture: mixing the solvent-filler mixture with the powder resin to create a composite; pouring the composite into a mold; pressing the mold with the composite therein by compression, wherein the mold comprises an opening to release extra composite from the mold; and setting the molds with the compressed composite therein to form the dental material. In another embodiment, the method includes milling the dental material to form a dental restoration.

Embodiments of the present invention are also directed to a method of preparing a dental material comprising: sonically mixing at least one filler with a solvent to form a filler-solvent mixture, wherein the at least one filler comprises at least one selected from the group of boron nitride and zirconia, wherein the boron nitride is in hexagonal form with particles having an average particle size of between about 10 nm and about 800 nm and the zirconia has an average particle size of between about 20 nm and about 800 nm; mixing the filler-solvent mixture with a powder resin to form a composite; and preparing the composite into a dental material by pressing and setting the composite in a mold. In another embodiment, the method includes milling the dental material into a dental restoration.

These objects and other advantages are accomplished by the compositions and methods of fabrication described herein. Objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention.

DETAILED DESCRIPTION OF THE INVENTION

Embodiments of the present invention are directed to high-strength high-stiffness structural compositions for use in dental applications, more particularly, a dental material that can be milled into a dental restoration for installation in a patient.

The term "dental restoration" shall mean any structure for placement in the mouth of a patient or component thereof, including but not limited to provisional or temporary restorations such as inlays, crowns, bridges, and repairs. The abbreviations "gm" or "g" shall refer to grams. The abbreviations "ml" or "mL" shall refer to milliliter. The abbreviation "gf" shall refer to gram force. The abbreviation "nm" shall refer to nanometer.

Figure 1:
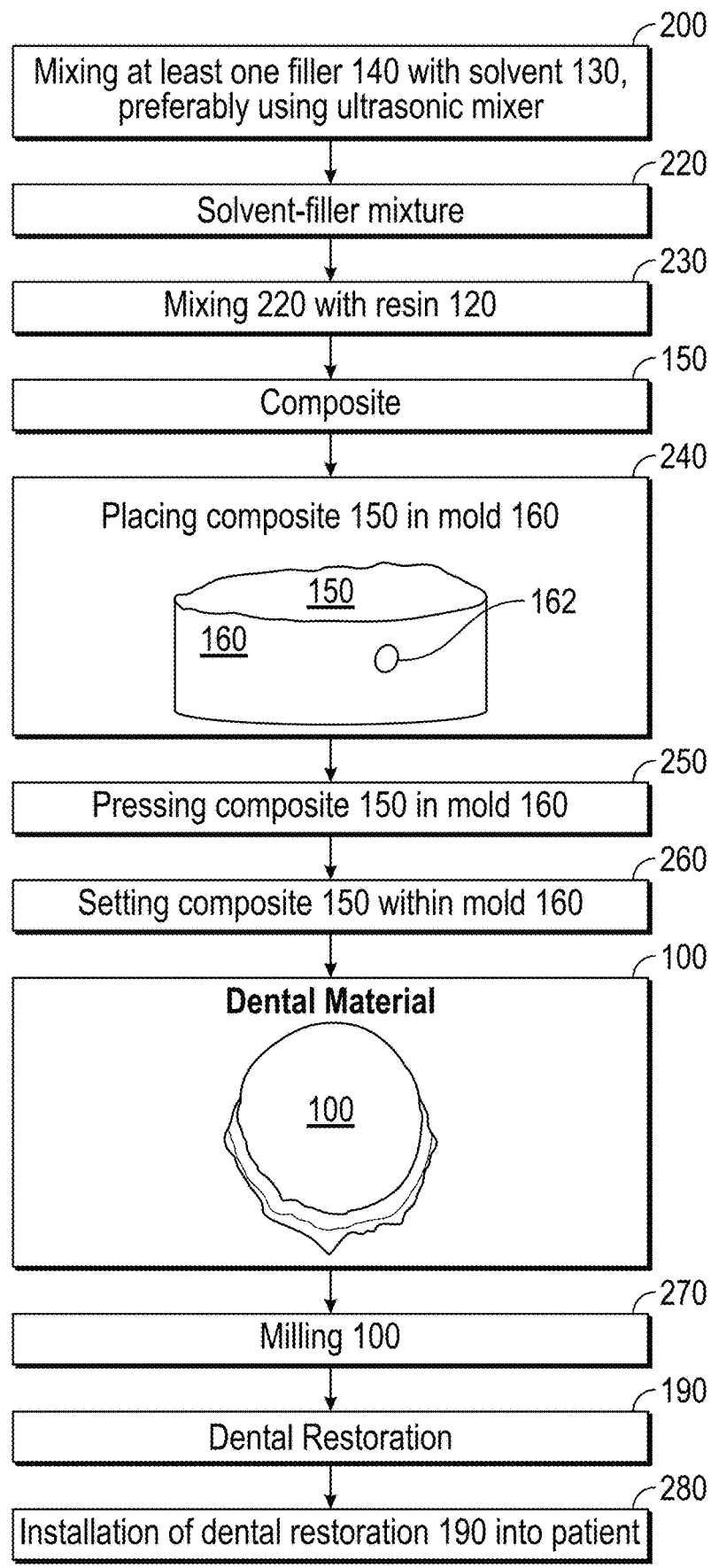
FIG. 1 is a flow chart illustrating the steps of a method of preparing a dental material for milling and installation as a dental restoration in the mouth of a patient, according to an embodiment of the present invention.
Figure 2:
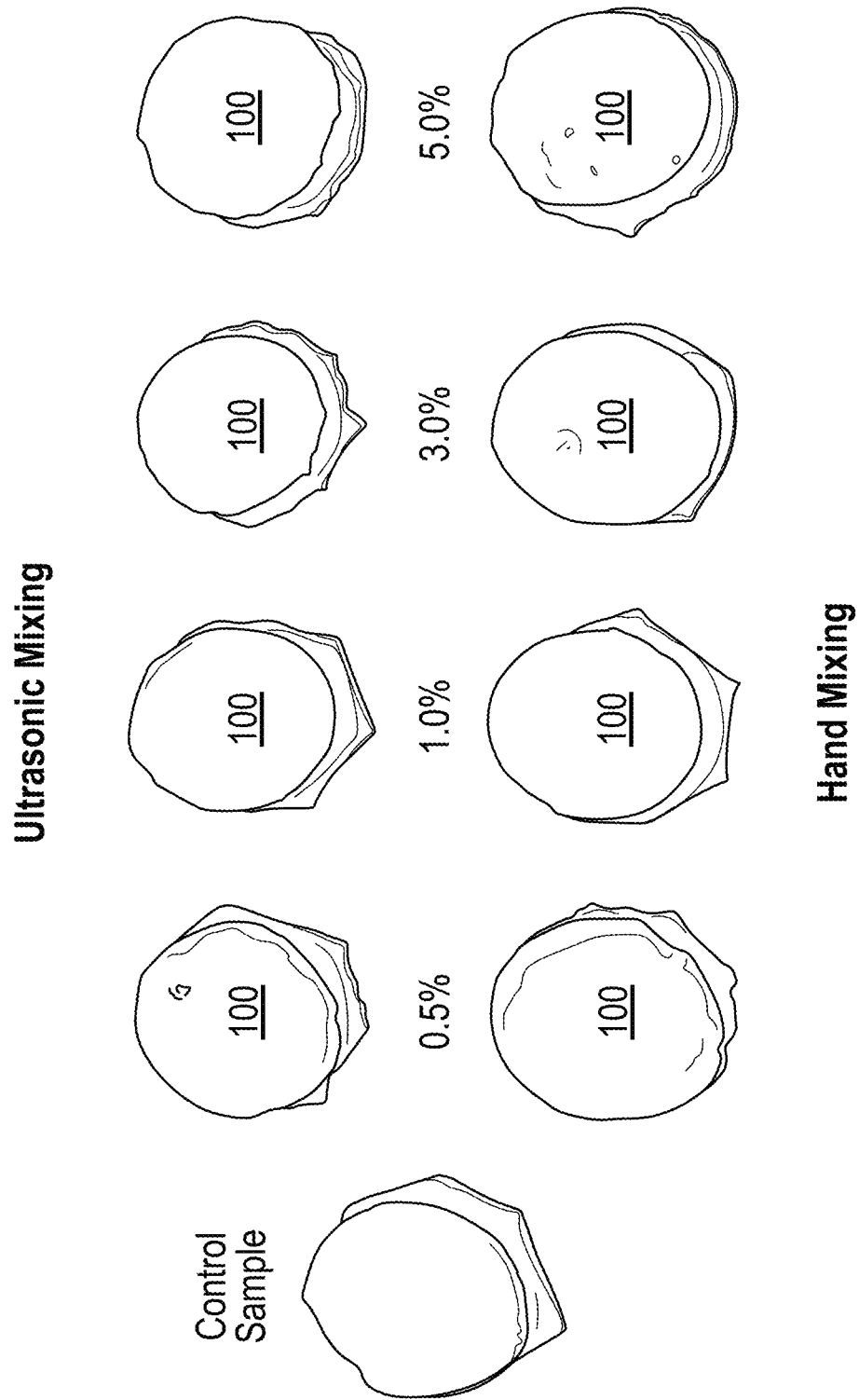
FIG. 2 is an illustration of specimens of dental material made by mixing nano-sized h-BN powder reinforcement with different concentrations into PMMA materials according to an embodiment of the present invention.

Referring to FIGS. 1 and 2, in an embodiment of a dental material 100 according to the present invention, the dental material 100 preferably comprises a resin 120 mixed with a solvent 130 and a filler 140 and/or combination of fillers 140. Preferably, dental material 100 comprises at least one of the two following fillers: boron nitride 142 and zirconia 143 (hereinafter sometimes referred to as "filler" or "fillers"). In some embodiments, dental material 100 comprises only boron nitride 142 as a filler, along with resin 120 and solvent 130. In other embodiments, dental material 100 comprises only zirconia 143 as a filler, along with resin 120 and solvent 130.

Preferably, filler 140 comprises boron nitride 142 in hexagonal form (h-BN), although it should be recognized that amorphous boron nitride can also be used. In another embodiment, boron nitride filler 140 comprises a Wurtzite form, preferably hexagonal Wurtzite. In one embodiment of dental material 100, boron nitride filler 142 is of a high purity, preferably comprising at least about 50% purity of h-BN, more preferably at least about 75% and most preferably at least about 99%. Different sized particles of h-BN can be used depending on the desired result. In one embodiment, the h-BN particles have an average particle size (APS) of about 10 nm. In another embodiment, they have an APS of between about 5 nm and about 15 nm. In another embodiment, they have an APS of about 70 nm. In another embodiment, they have an APS of about 60 nm to about 80 nm. In another embodiment, they have an APS of about 800 nm. In another embodiment, they have an PAS of about 700 nm to about 900 nm. Preferably, the h-BN particles have an APS of between about 10 nm and about 1000 nm and most preferably between about 70 nm and about 800 nm. Preferably, dental material 100 comprises a mixture of about 0.25% to about 10% by weight of h-BN, and most preferably between about 0.5% and about 5.0% by weight of h-BN.

Preferably, filler 140 comprises a zirconia 143 that is stabilized, including but not limited to $ZrO_2$-8Y. It should be noted that embodiments of the present invention also comprise normal zirconia that is not stabilized; stabilized zirconia is not required for the invention to function as intended. In one embodiment of dental material 100, zirconia filler 143 is of a high purity, preferably comprising at least about 50% purity of zirconia, more preferably at least about 75% and most preferably at least about 99%. Different sized particles of zirconia 143 can be used depending on the desired result. In one embodiment, the zirconia particles have an APS of about 20 nm. In another embodiment, the zirconia particles have an APS of about 10 nm to about 30 nm. In another embodiment, they have an APS of 800 nm. In another embodiment, the zirconia particles have an APS of about 700 nm to 900 nm. Preferably, the zirconia particles have an APS of between 10 nm and about 1000 nm and most preferably between about 20 nm and about 800 nm. Preferably, dental material 100 comprises a mixture of about 0.50% to about 20% by weight of zirconia, and most preferably about 1.0% to about 10% by weight of zirconia.

Resin 120 is preferably a powder and solvent 130 is preferably a liquid. The ratio of powder resin 120 to liquid solvent 130 depends on the desired properties of dental material 100. In one embodiment, the powder resin 120 to liquid solvent 130 ratio is 1 gm of powder to 0.5 ml of liquid (1 scale of powder to 1 scale of liquid). Preferably, the powder resin 120 to liquid solvent 130 ratio is between about 2.0 gm of powder to 1.0 ml of liquid and about 2.0 gm of powder to 2.0 ml of liquid, and most preferably between about 2.0 gm of powder to 1.0 ml of liquid and 2.0 gm of powder to 1.5 ml of liquid. In some embodiments, resin 120 is in the form of a paste.

Resin 120 is preferably a self-curing acrylic resin, for example a UNIFAST III™ resin powder, comprising an ethyl-methyl methacrylate polymer and a polymethylmethacrylate.

Solvent 130 is preferably a liquid monomer, for example a UNIFAST III™ liquid solvent. Solvent 130 preferably comprises: methyl methacrylate, N,N-dimethyl-p-toluidine; ethyleneglycol dimethacrylate; and/or trimethylolpropane trimethacrylate.

In one embodiment of dental material 100 according to the present invention, dental material 100 comprises a mixture of resin powder 120, liquid solvent 130 and hBN 142 and Zirconia 143 fillers in about the proportions stated as follows in percentage by weight:
  UNIFAST III Powder comprising about >70% Ethyl-methyl methacrylate polymer and about <30% Polymethylmethacrylate;
  UNIFAST III Solvent comprising about 92.0% Methyl methacrylate, about 4.0% N,N-dimethyl-p-toluidine, about 2.0% Ethyleneglycol dimethacrylate and about 1.8% Trimethylolpropane trimethacrylate;
  Hexagonal boron nitride, the particles of which are about 70 nm and 800 nm in size and a concentration of up to about 5.0 wt. %; and
  Zirconia, the particles of which are about 20 nm and 800 nm in size and a concentration of up to about 10.0 wt,%.

Not all embodiments of dental material 100 comprise both hexagonal boron nitride and zirconia fillers. In one embodiment of dental material 100, hexagonal boron nitride is the only filler. In another embodiment, zirconia is the only filler. The concentration of each filler 140 when both or each alone is used is adjusted according to the desired properties of the final composition.

Embodiments of the present invention are also directed to methods of making dental material 100 and making a dental restoration 190 therefrom. The various compositions described above are not limited to the methods of making them described herein. The methods of making the compositions described herein are only preferred examples of how to make the compositions.

Referring to FIG. 1, preferably, either or both of the fillers 140 hexagonal boron nitride 142 and zirconia 143 are first mixed with the solvent before mixing with the resin powder 120, to provide a more complete polymerization. That is, prior to mixing any fillers 140 with resin 120, a solution of filler 140 is preferably mixed in solvent 130 and sonicated to completely disperse the nanoparticles of filler 140, or at least to disperse the filler 140 an adequate amount for the desired characteristics for dental material 100. Creating solvent-filler mixture 220 before mixing filler 140 with resin 120 solves or alleviates the problem of agglomeration of filler 140 described above. For example, in one embodiment illustrated in FIG. 1, hexagonal boron nitride 142 is mixed with solvent 130 alone using an ultrasonic homogenizer in a sonicating step 200, creating a solvent-filler mixture 220 of a desired homogenization. Various states of homogenization are described in the examples provided later in this application, the state of homogenization informed in party by the amount of time of mixing and the power of the mixing device (and depending on whether by hand or using an ultrasonic mixer). If hand mixing, for example by using a plastic spatula, it is preferable to mix filler 140 with solvent 130 for between about 1 second to about one minute, more preferably about 5 seconds to about thirty seconds, and most preferably about ten seconds to about 15 seconds. If using an ultrasonic mixer, it is preferable to mix filler 140 with solvent 130 for between about 5 seconds to about 90 seconds, more preferably about 10 seconds to one minute, and most preferably about 20 seconds to about 30 seconds.

Preferably, solvent-filler mixture 220 is mixed with resin 120 in resin mixing step 230 to create composite 150. In one embodiment, solvent-filler mixture 220 is mixed with resin 120 by hand. In another embodiment, solvent-filler mixture 220 is mixed with resin 120 using an ultrasonic homogenizer. In another embodiment, hexagonal boron nitride 142 is mixed with resin 120 and solvent 130 by hand. In one method of making dental material 100, the resin 120 and solvent 130 are mixed in the proportions described above with the hexagonal boron nitride and zirconia fillers. In one embodiment, the filler 140 is not mixed first with solvent 130 but rather all of filler 140, solvent 130 and resin 120 are mixed together without first creating solvent-filler mixture 220. Various other methods and techniques of mixing the resin 120, solvent 130 and at least one filler 140 to create composite 150 according to the present invention are described in the examples provided herein. This mixing preferably continues until composite 150 reaches its desired consistency. The desired consistency of composite 150 is preferably a soft dough-like consistency, that is, malleable and/or kneadable or that maintains its shape when no force is applied to it. Preferably, the mixing is complete once composite 150 passes the three following stages of mixing/homogenization: 1) sandy stage; 2) stingy stage in which the mixture is sticky and adheres to the sides of the rubber cup, Pyrex beaker, and the mixing vessel (or the tip of the ultrasonic mixer or the plastic spatula used in hand mixing); and 3) smooth dough-like stage, that is, when the composite is more cohesive and does not adhere to the sides of the rubber cup, Pyrex beaker, and the mixing vessel, so it can then be poured in the mold.

Once composite 150 reaches the desired consistency, composite 150 is preferably poured into mold 160 or any number of molds 160 depending on the volume of composite 150 and the desired number of dental restorations 190. Preferably, composite 150 is poured into mold 160 within enough time to avoid any amount of time passing without any mixing occurring that might cause composite 150 to settle, separate, harden, or otherwise change into an undesired state or shape.

Preferably, molds 160 are shaped in the form of a disc so that a compression molding technique can be employed to press composite 150. In one embodiment, mold 160 is preferably a disc of about 15 mm in diameter and about 3 mm thick. For dental applications, preferably the disc mold 160 are sized about 10 mm in diameter to about 50 mm in diameter, more preferably about 50 mm in diameter to about 100 mm in diameter and most preferably about 10 mm in diameter to about 100 mm in diameter, and the thickness of the disc if preferably between about 1 mm and 40 mm but most preferably between about 0.75 mm and 15 mm.

In some embodiments, molds 160 are shaped as a block or a cube. Preferably block mold 160 are sized large enough for milling into a dental restoration. Preferably, the blocks are sized between about 40×19×15 mm and about 55×15.5×19 mm.

Preferably mold 160 comprises a material with a high tear resistance, for example Teflon. In some embodiments, mold 160 comprises silicone, stainless steel, titanium and/or various combinations thereof.

Once composite 150 is in mold 160, preferably at least one end of mold 160 is provided with an opening 162 to release extra composite 150 from mold 160 during the pressing process 250. Preferably, molds 160 are pressed by compression in pressing process 250. In one embodiment, the compression molding technique of the pressing step 250 comprises placing molds 160 containing composite 150 between two plates (for example, of glass) and pressing molds 160 between the glass plates. Preferably, the compression applies just enough force to squeeze the composite 150 in each mold 160 until composite 150 is of a desired density. The shapes of mold 160 relate to the method of pressing. In some embodiments of the present invention, other methods of pressing are employed and the shape of mold 160 is altered accordingly. Referring to mold 160 as having a top, bottom and at least one side, in one embodiment, opening 162 is disposed on a side of mold, such that, when plates are disposed on the top and bottom of mold 160, opening 162 is able to release composite 150 pushed out of the mold by the pressing process. Mold 160 may have any number of openings 162.

After the pressing step 250 is complete, that is, once the composite 150 has the desired density within each mold 160, the extra composite 150 that exited the molds through openings 162 is preferably removed, for example by using a razor blade to separate the extra composite from the composite in the mold. Then molds 160 with the composite 150 therein are set in a setting process 260, preferably by self-curing, a method of thermal setting.

After the setting process 260 is complete, composite 150, now shaped, is referred to as dental material 100 and is released from molds 160 and can be milled in a milling step 270 to the desired shape and orientation of the desired final dental restoration 190. In some embodiments, dental material 100 is then subsequently milled in a milling step 270 to make a specific dental restoration 190 using, for example, Computer Aided Design/Computer Aided Manufacture (CAD/CAM). Dental restoration 190 can then be installed into the patient.

Dental material 100 can also be described by its mechanical characteristic Vickers hardness, Young's modulus and flexural strength, as the various examples provided below show in providing results of various testing of dental materials prepared according to the present invention. In some embodiments of the dental material and method of preparing the dental material, the Vickers hardness of the dental material increases at least about 60% under ultrasonic mixing. In another embodiment, the Vickers hardness of the dental material increases at least about 150% when adding about 5.0 wt % of boron nitride fillers. In another embodiment, the Vickers hardness of the dental material increases at least about 300% when adding about 5.0 wt % of boron nitride fillers. In another embodiment, the flexural strength of the dental material increases at least about 550% when adding about 5.0 wt % of boron nitride fillers. In another embodiment, the Young's Modulus of the dental material increases at least about 240% when adding about 5.0 wt % of boron nitride fillers. In another embodiment, the Vickers hardness of the dental material increases at least about 400% when adding about 5.0 wt % of zirconia and at least about 600% when adding about 10.0 wt % of zirconia. In another embodiment, the flexural strength of the dental material increases at least about 280% when adding about 5.0 wt % of zirconia and at least about 800% when adding about 10.0 wt % of zirconia. In another embodiment, a Young's Modulus of the dental material increases at least about 140% when adding about 5.0 wt % of zirconia and at least about 250% when adding about 10.0 wt % of zirconia.

EXAMPLES

The invention is further illustrated by the following non-limiting examples.

Example 1

A dental material 100 according to an embodiment of the present invention was made to contain the following percentages by weight of components:
UNIFAST III Powder:
>70% Ethyl-methyl methacrylate polymer
<30% Polymethylmethacrylate
UNIFAST III Solvent:
92.0% Methyl methacrylate
4.0% N,N-dimethyl-p-toluidine
2.0% Ethyleneglycol dimethacrylate
1.8% Trimethylolpropane trimethacrylate
Hexagonal boron nitride, 70 nm and 800 nm in size and concentration up to 5.0 wt. %.
Zirconia, 20 nm and 800 nm in size and concentration up to 10.0 wt. %.

Example 2

Dental material 100 described in Example 1 was made according to the following method, which is one embodiment of a method of the present invention.

Specimens of dental material 100 were made by mixing the resin UNIFAST III powder with UNIFAST liquid monomer, both from GC Corporation (Tokyo, Japan). The standard powder to liquid ratio was 1 gm of powder to 0.5 ml of liquid (1 scale of powder to 1 scale of liquid), however the powder to liquid ratio is adjustable between 2 gm:1 ml and 2 gm:1.5 ml. Both hand and ultrasonic mixing techniques were carried out. The hand mixing was made exactly as routinely performed at a dental office, where powder and liquid monomer are put together in a rubber cup and hand mixed for 10-15 second using a plastic spatula. The ultrasonic mixing is carried out by using high power Ultrasonic Homogenizer Sonicator Cell Disruptor Mixer 450 W max 10-300 ml. The power of the ultrasonic homogenizer was kept between 5% and 50% of maximum power for a mixing time between 10 s and 30 s. When the mixture reached a soft dough stage, it was immediately poured into 15 mm diameter by 3 mm thick disc shape Teflon molds, which provides extremely high tear resistance. Both ends of the mold were opened (provided with holes). Compression molding was performed by pressing the specimens between two plates made of glass. The discs were then released after thermal setting of the composites while the extra material was removed using a razor blade between each compression.

For the boron nitride reinforcement fillers, 99.8% purity h-BN nanoparticles, 70 nm and 800 nm in size were from US Nanomaterials Co., Ltd.—USA. The proper loadings of BN nanofillers for each mixture were measured using an available Uuni-WT 100×0.1 micro gram Analytical Balance Lab with Digital Scale Range. We made typical mixtures of 0.5, 1.0, 3.0, and 5.0% by weight (wt.) of loading nanoparticles into UNIFAST III powder-based solution.

For the Zirconia reinforcement fillers, stabilized zirconia ZrO2-8Y, 20 nm and zirconia ZrO2, 20 nm and 800 nm in size were also from US Nanomaterials Co., Ltd.—USA, both with purity 99.95%. We made typical mixtures of 1.0, 2.0, 3.0, 5.0, 7.0, and 10.0% by weight (wt.) of loading nanoparticles into UNIFAST III powder-based solution.

Since nanoparticles agglomerate easily due to high surface energy and many conventional techniques cannot break-up their agglomerates, making well dispersed discrete nanoparticles in polymer films is the key issue to achieving higher mechanical performance. So, prior to mixing filler nanoparticles with the powder, a solution of nanoparticles in GC UNIFAST liquid solvent was sonicated to completely disperse the nanoparticles, or at least, to disperse the nanoparticles to the desired dispersion for the desired results. We also made unloaded or control samples for comparison purpose.

The fact that the h-BN, ZrO2-8Y, and ZrO2 are present in non-agglomerated form can be demonstrated, for example, by means of scanning electron microscopy (SEM). The average size of the particles is also measured by means of SEM. The nanocomposite formation can be demonstrated by means of X-ray diffraction (XRD) and Fourier transform infrared spectrometry (FTIR). It is observed that XRD intensity of the peaks increases with the increase of nanoparticles concentration. It is found that specimens made by hand and ultrasonic mixing do not show similar FTIR spectrum. The spectrum of the specimen made by hand mixing is much like the one taken on pure UNIFAST ill powder. This could be a sign that polymerization of the powder under liquid monomer is not fully complete as compared to specimen made by ultrasonic mixing.

Various methods of mixing were performed, as described in the following examples.

Mixing Example 1: Hand mixing of unfilled dental material. About 2 gm of UNIFAST III powder and about 1 ml of UNIFAST liquid monomer solvent were put together in a rubber cup and hand mixed for about 10 seconds using a plastic spatula.

Mixing Example 2: Ultrasonic mixing of unfilled dental material. About 4 gm of UNIFAST III powder and about 2 ml of UNIFAST liquid monomer solvent were put together in a Pyrex beaker and mixed by using high power Ultrasonic Homogenizer at power of about 15% for about 20 seconds.

Mixing Example 3: Hand mixing using BN 70 nm nanoparticles fillers. About 2 gm powder UNIFAST III powder and about 1 ml monomer UNIFAST solvent and 10 mg BN 70 nm in size, which is equivalent to about 0.5 wt. % of BN in UNIFAST III powder, were put together in a rubber cup and hand mixed for about 10 seconds using a plastic spatula.

Mixing Example 4: Hand mixing using BN 800 nm nanoparticles fillers. About 2 gm powder UNIFAST III powder and about 1 ml monomer UNIFAST solvent and about 20 mg BN 800 nm in size, which is equivalent to about 1.0 wt. % of BN in UNIFAST III powder, were put together in a rubber cup and hand mixed for about 10 seconds using a plastic spatula.

Mixing Example 5: Ultrasonic mixing using BN 70 nm fillers. About 4 gm of UNIFAST III powder in a first Pyrex beaker. About 2 ml monomer UNIFAST solvent was put in a second Pyrex beaker. A 120 mg BN 70 nm in size, which is equivalent to 3.0 wt. % of BN, was added to the solvent and mixed together by using high power Ultrasonic Homogenizer at power of about 10% for about 15 seconds. The solution was poured in the first Pyrex and mixed together by using high power Ultrasonic Homogenizer at power of about 15% for about 20 seconds.

Mixing Example 6: Ultrasonic mixing using BN 800 nm fillers. About 4 gm of UNIFAST III powder were placed in a first Pyrex beaker. About 2 ml monomer UNIFAST solvent was put in a second Pyrex beaker. About 200 mg of BN 800 nm in size, which is equivalent to about 5.0 wt. % of BN, was added to the solvent and mixed together by using high power Ultrasonic Homogenizer at power of about 10% for about 15 seconds. The solution was poured in the first Pyrex and mixed together by using high power Ultrasonic Homogenizer at power of 15% for about 20 seconds.

Mixing Example 7: Hand mixing using ZrO2-8Y 20 nm fillers. About 2 gm of UNIFAST III powder and about 1 ml monomer UNIFAST solvent and about 40 mg ZrO2-8Y 20 nm in size, which is equivalent to 2.0 wt. % of ZrO2-8Y in UNIFAST III powder, were put together in a rubber cup and hand mixed for about 10 seconds using a plastic spatula.

Mixing Example 8: Ultrasonic mixing using ZrO2-8Y 800 nm fillers. About 2 gm of UNIFAST III powder was placed in a first Pyrex beaker. About 1 nil of monomer UNIFAST solvent was put in a second Pyrex beaker. About a 140 mg ZrO2-8Y 800 nm in size, which is equivalent to about 7.0 wt. % of ZrO2-8Y, was added to the solvent and mixed together by using high power Ultrasonic Homogenizer at power of about 10% for about 15 seconds. The solution was poured in the first Pyrex and mixed together by using high power Ultrasonic Homogenizer at power of about 20% for about 25 seconds.

Mixing Example 9: Hand mixing using ZrO2 20 nm fillers. 2 gm powder UNIFAST III powder+1 ml monomer UNIFAST solvent+200 mg ZrO2 20 nm in size, which is equivalent to 10.0 wt. % of ZrO2 in UNIFAST III powder, were put together in a rubber cup and hand mixed for 15 seconds using a plastic spatula.

Mixing Example 10: Ultrasonic mixing using ZrQ2 800 nm fillers. About 2 gm of UNIFAST III powder was placed in a first Pyrex beaker, About 1 ml monomer UNIFAST solvent was put in a second Pyrex beaker. About a 200 mg ZrO2 800 nm in size, which is equivalent to about 10.0 wt. % of ZrO2-8Y, was added to the solvent and mixed together by using high power Ultrasonic Homogenizer at power of about 10% for about 15 seconds. The solution was poured in the first Pyrex and mixed together by using high power Ultrasonic Homogenizer at power of about 25% for about 30 seconds.

The micro-hardness characterization of the samples were investigated by Vickers hardness measurement technique using Vickers hardness tester Model: VH-5B. The specimen was prepared as per ASTM (American Society for Testing of Materials) standards, then it was polished in a polishing machine using rough polishing and fine polishing using fine polishing paste of 3 micron grade, after getting micro polishing specimen were tested by a hardness testing machine to determine the Vickers micro hardness number by using a diamond indenter of few microns diameter. The indenter was made to strike the specimen samples for varying loadings. In each measurement the indenter was allowed to strike the sample for a period of 20 seconds, then the average indentation diameter (average of both diagonals of the indenter) of the sample was recorded using the travelling microscope attached to the testing machine. The Vickers hardness number in Kg/mm2 was calculated using the following formula (referred to herein as "Formula 1"):

$$HV = \left(\frac{1.854f}{d^2}\right)$$

Where f was the applied force in Kgf and d was the diagonal indentation length in micrometer. To convert HV to MPa, we multiplied recorded values by 9.807. The Vickers hardness (VH) measurements on specimens made by hand and ultrasonic mixing methods included the control sample and nano-sized h-BN, ZrO2-8Y, and ZrO2 reinforced samples with different concentration.

After manufacturing, each group of specimens were cut out of blocks with a diamond saw to enable measurements of the flexural strength. All bending bars (3×2.5 mm) were polished using diamond-embedded wheels of 45 μm grit size with water running and then to 2.5 and 1 μm with polycrystalline diamond paste. The flexural strength of the specimens was evaluated via a three-point bending test with an across head speed of 0.4 mm/min. The load and the corresponding deflection were recorded. The flexural strength was calculated using the following formula (referred to herein as "Formula 2"):

$$\delta_f = \left(\frac{3fl}{2wh^2}\right)$$

Where f=load at fracture
l=span tested (here 8 mm)
w=width of the specimen
h=height of the specimen The Young's modulus of the specimens was evaluated via a standard uniaxial state of stress testing method which is normally used for uniform and homogeneous materials. Applying tension loads introduces stress in the object, thus increasing the initial length of the test specimen. The rate of this increase determines the modulus of elasticity also known as Young's modulus (E or Y). Young's modulus is generally calculated using the Hooke's law for uniaxial stress which can be expressed as the following formula (referred to herein as "Formula 3"):

$$\frac{F}{A} = E\frac{\Delta L}{L_0}$$

F is the tensile force applied to the object (unit Newton)
A is the area of cross section (m$^2$)
E is the Young's modulus (Pa)
$\Delta L$ is the deformation length
$L_0$ is the original clamped length without load (m)

When h-BN according to the invention was used as a filler, VH hardness initially increased with increasing load indicating the material resistance to plastic deformation. Then, VH stabilized around a certain value (plateau region) at a load of 160 gf which defined the hardness value of the material beyond which the mechanical breakdown of the materials takes place at a load of 225 gf. The table below includes measured data on micro hardness, flexural strength, and bulk modulus carried on fabricated specimens. According to Material Property Database of pure PMMA, the hardness, flexural strength, and Young's modulus are within range.

The Vickers Hardness, Flexural Strength, and Young Modulus for the samples were recorded as stated in the following table (referred to herein as Table 1):

| Filler | wt %. | Vickers Hardness (MPA) | | Flexural Strength (MPA) | | Young Modulus (MPA) | |
|---|---|---|---|---|---|---|---|
| | | Hand mixing | Ultrasonic mixing | Hand mixing | Ultrasonic mixing | Hand mixing | Ultrasonic mixing |
| h-BN (70 nm) | 0 | 617 | 1019 | 50 | 65 | 1467 | 1758 |
| | 0.5 | 765 | 1235 | 74 | 94 | 1829 | 1920 |
| | 1 | 868 | 1510 | 90 | 128 | 1950 | 2209 |
| | 3 | 1020 | 1667 | 144 | 206 | 2209 | 2645 |
| | 5 | 1167 | 1863 | 192 | 276 | 2438 | 3078 |
| h-BN (800 nm) | 0.5 | 1402 | 1961 | 82 | 104 | 2043 | 2196 |
| | 1 | 1530 | 2079 | 162 | 232 | 2658 | 3375 |
| | 3 | 1569 | 2275 | 192 | 274 | 3392 | 4211 |
| | 5 | 2040 | 2569 | 230 | 329 | 3850 | 5032 |
| ZrO2-8Y (20 nm) | 1 | 1274 | 2285 | 78 | 114 | 1629 | 1938 |
| | 2 | 1863 | 2765 | 95 | 144 | 1756 | 2033 |
| | 3 | 2422 | 2981 | 123 | 167 | 1841 | 2210 |
| | 5 | 2549 | 3069 | 139 | 190 | 1938 | 2381 |
| | 7 | 2755 | 3138 | 183 | 220 | 2210 | 2640 |
| | 10 | 4030 | 4550 | 345 | 449 | 3841 | 4590 |
| ZrO2 (800 nm) | 1 | 1206 | 1569 | 66 | 103 | 1841 | 2210 |
| | 2 | 1569 | 1961 | 96 | 128 | 2424 | 3443 |
| | 3 | 1667 | 2079 | 126 | 154 | 2758 | 3830 |
| | 5 | 1824 | 2275 | 162 | 206 | 3303 | 4241 |
| | 7 | 2039 | 2569 | 192 | 232 | 4216 | 4715 |
| | 10 | 2245 | 2814 | 238 | 275 | 4778 | 5232 |

Referring to Table 1, it was found that recorded VH hardness was 1019 MPa versus 617 MPa for control specimens prepared by ultrasonic and hand mixing methods, respectively. This is translated to a more than 65% increase in the hardness value when using ultrasonic mixing (see FIG. 10). For specimens loaded with nano-sized h-BN powder, VH values increased with the increasing of h-BN fillers concentration. For specimens prepared by ultrasonic mixing, VH values reached 1863 MPa when using h-BN 70 nm (FIG. 10) and a value of 2569 MPa when using h-BN 800 nm in size at a concentration of 5.0 wt % (FIG. 11). For specimens prepared by hand mixing, VH hardness reached a value of 2040 MPa versus 617 MPa when using same filler and same concentration. We can state that when using ultrasonic mixing method combined with nano-sized h-BN powder VH hardness increases to more than 310% with respect to the unmodified sample made by hand mixing. FIG. 11 depicts the VH hardness measurements versus h-BN composition in PMMA on specimens made by both hand and ultrasonic mixing methods. It shows that using ultrasonic mixing method combined with nano-sized h-BN powder, increases the VH hardness to 300% with respect to the unmodified sample made by hand mixing.

When h-BN according to the invention was used as a filler, the stiffness strength (FS) initially increases with increasing load indicating the material degree of rigidity. Recorded stiffness strength values were 65 MPa versus 50 MPa for control specimens prepared by ultrasonic and hand mixing methods, respectively. However, it was 329 MPa when using h-BN 800 nm in size at a concentration of 5.0 wt %. This corresponded to an increase in FS of more than 550%.

When h-BN according to the invention was used as a filler, the modulus of elasticity or Young's modulus (YM) initially increased with increasing load indicating the material ability to withstand compression and tension. Recorded Young's modulus values are 1758 MPa versus 1467 MPa for control specimens prepared by hand mixing. However, it was 5032 MPa when using h-BN 800 nm in size at a concentration of 5.0 wt %. This corresponded to an increase in YM of more than 240%.

When ZrO2-8Y was used as a filler, VH hardness initially increased with increasing load indicating the material resistance to plastic deformation. For specimens loaded with nano-sized h-BN powder, VH hardness increased with the increasing of ZrO2-8Y fillers concentration. For specimens prepared by ultrasonic mixing, VH hardness reached a value of 3069 MPa when using 20 nm in size ZrO2-8Y at a concentration of 5.0 wt %. This corresponded to an increase in VH hardness of about 200%. For specimens prepared by hand mixing, VH hardness reached a value of 2549 MPa versus 617 MPa when using same filler and same concentration. We can state that when using an ultrasonic mixing method combined with 20 nm in size and 5.0 wt % in weight of ZrO2-8Y powder, VH hardness increased to about 400% with respect to the unmodified sample made by hand mixing. The increase reached more than 600% in case 10.0 wt % of the same filler is used.

When ZrO2-8Y was used as a filler, the stiffness strength (FS) initially increased with increasing load indicating the material degree of rigidity. FS is 190 MPa for specimen prepared by ultrasonic mixing of ZrO2-8Y 20 nm in size at a concentration of 5.0 wt %. With respect to hand mixing sample, this corresponded to an increase in FS of about 280% and can reach more than 800% at a concentration of 10.0 wt % of the same filler.

When ZrO2-8Y was used as a filler, the modulus of elasticity or Young's modulus (YM) initially increased with increasing load indicating the material ability to withstand compression and tension. YM is 2381 MPa for specimen prepared by ultrasonic mixing of ZrO2-8Y 20 nm in size at a concentration of 5.0 wt %. This corresponded to an increase in YM of more than 60% and it can reach more than 200% at a concentration of 10.0 wt % of the same filler.

VH hardness increased with the increasing of ZrO2 fillers concentration. For specimens prepared by ultrasonic mixing, VH hardness reached a value of 2275 MPa when using 800 nm in size ZrO2 at a concentration of 5.0 wt %. This corresponded to an increase in VH hardness of more than 120%. For specimens prepared by hand mixing, VH hardness reached a value of 1824 versus 617 when using same filler and same concentration. We can state that when using ultrasonic mixing method combined with 800 nm in size ZrO2 powder VH hardness increases to more than 260% with respect to the unmodified sample made by hand mixing. This increase can reach more than 350% at a concentration of 10.0 wt % of the same filler.

When ZrO2 was used as a filler, the stiffness strength (FS) initially increased with increasing load indicating the material degree of rigidity. For specimens prepared by ultrasonic mixing, FS reached a value of 206 MPa when using 800 nm in size ZrO2 at a concentration of 5.0 wt %. This corresponded to an increase in FS of more than 300%. This increase can reach about 450% at a concentration of 10.0 wt % of the same filler.

When ZrO2 was used as a filler, the modulus of elasticity or Young's modulus (YM) initially increases with increasing load indicating the material ability to withstand compression and tension. For specimens prepared by ultrasonic mixing, YM is 4241 MPa when using ZrO2 800 nm in size at a concentration of 5.0 wt %. This corresponded to an increase in YM of more than 180%. This increase reached more than 250% at a concentration of 10.0 wt % of the same filler.

Accordingly, our records show that embodiments of the present invention can provide high strength high stiffness materials for making long-term dental inlays, crowns, bridges and repairs.

Figure 3A:
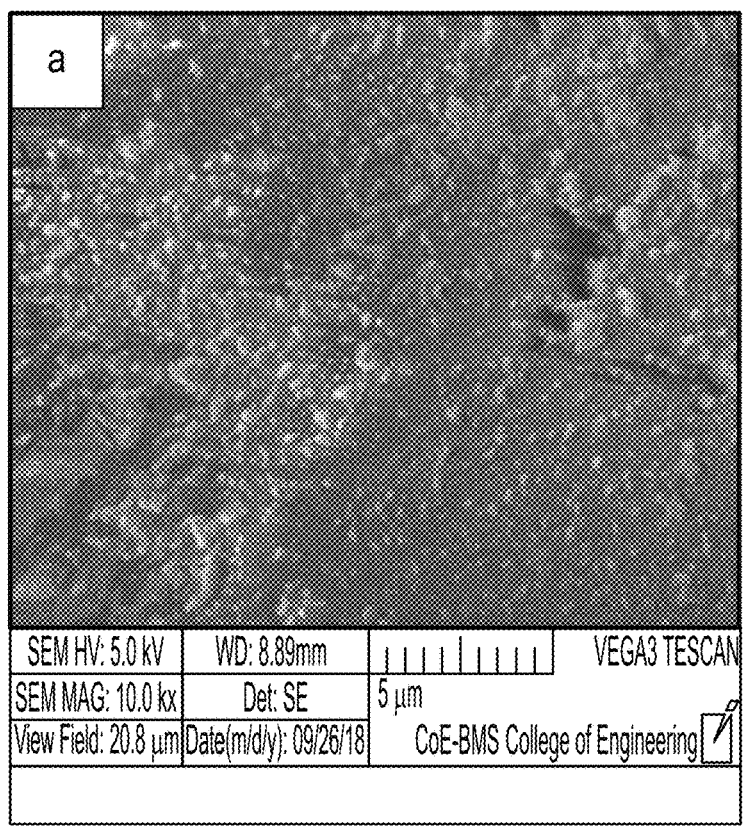
FIGS. 3A-3B are a series of SEM images of non-modified self-cured composite for hand mixing in FIG. 3A and for ultrasonic mixing in FIG. 3E, FIGS. 4A-4B are a series of SEM images showing high-resolution h-BN nanoparticles 50-70 nm used as reinforcement fillers and nanocomposite reinforced with 0.5 wt % of such nanoparticles under ultrasonic mixing, according to an embodiment of the present invention.
Figure 3B:
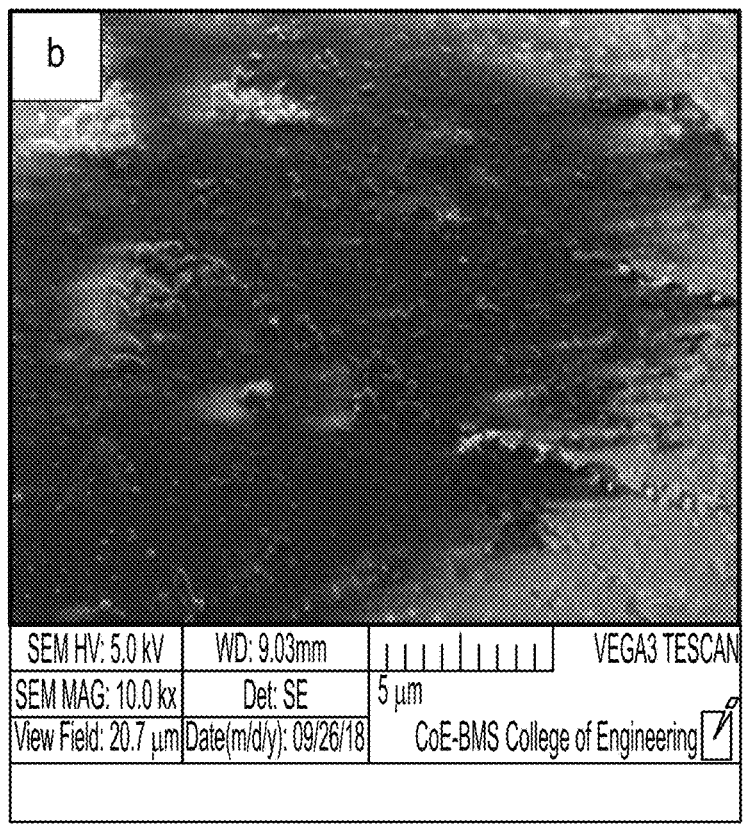
Figure 4A:
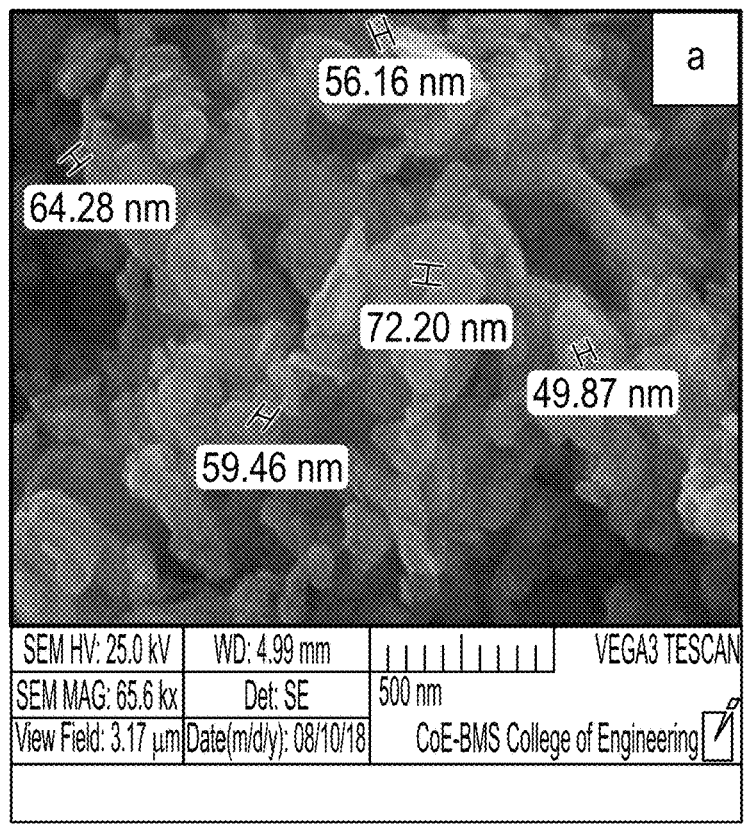
Figure 4B:
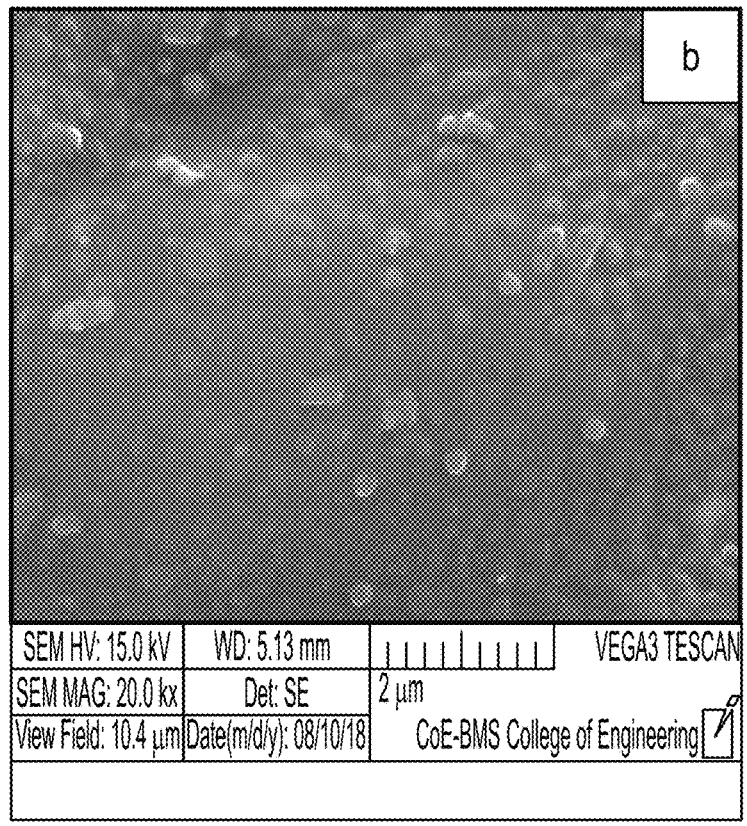

FIG. 2 shows the pictures of a typical control sample and specimens made by mixing nano-sized h-BN powder reinforcement with different concentration into PMMA materials. FIGS. 3A-3B show the SEM images of a typical non-modified self-cured composite for both hand and ultrasonic mixing. Apparently, and for same magnification, the ultrasonic mixing method provides better textures and packing density of the composite as compared to hand mixing.

FIGS. 4A-4E show the SEM images of the high-resolution h-BN nanoparticles 50-70 nm which were used as reinforcement fillers and the nanocomposite reinforced with 0.5 wt % of such nanoparticle under ultrasonic mixing. The fillers were expected to modify the structural and mechanical properties of the nanocomposites.

Figure 5A:
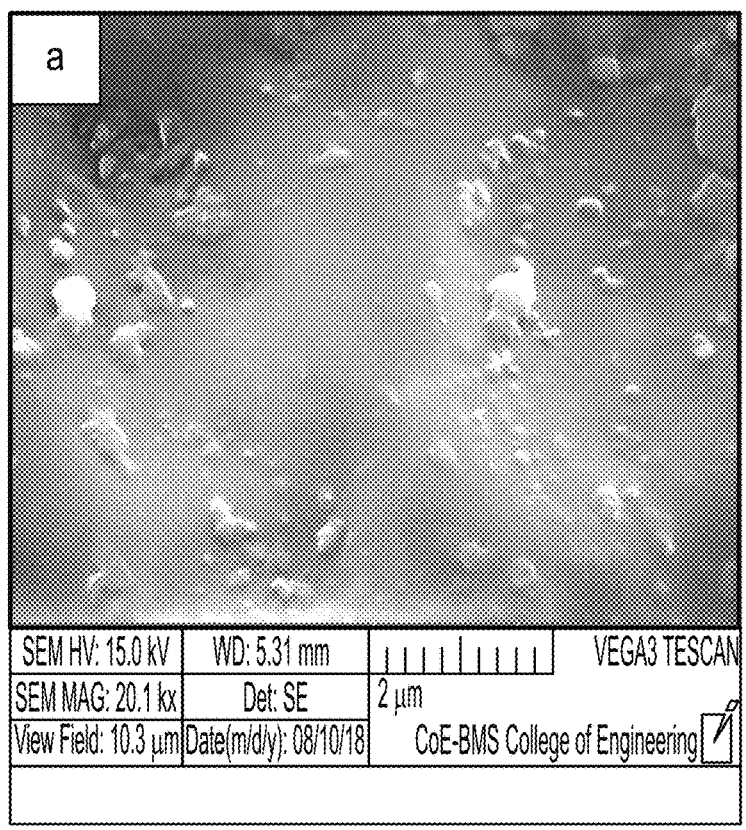
FIGS. 5A-5B are a series of SEM images of 1 wt % (FIG. 5A) and 5 wt % (FIG. 5B) self-cured PMMA/h-BN nanocomposites formed under ultrasonic mixing, according to an embodiment of the present invention.
Figure 5B:
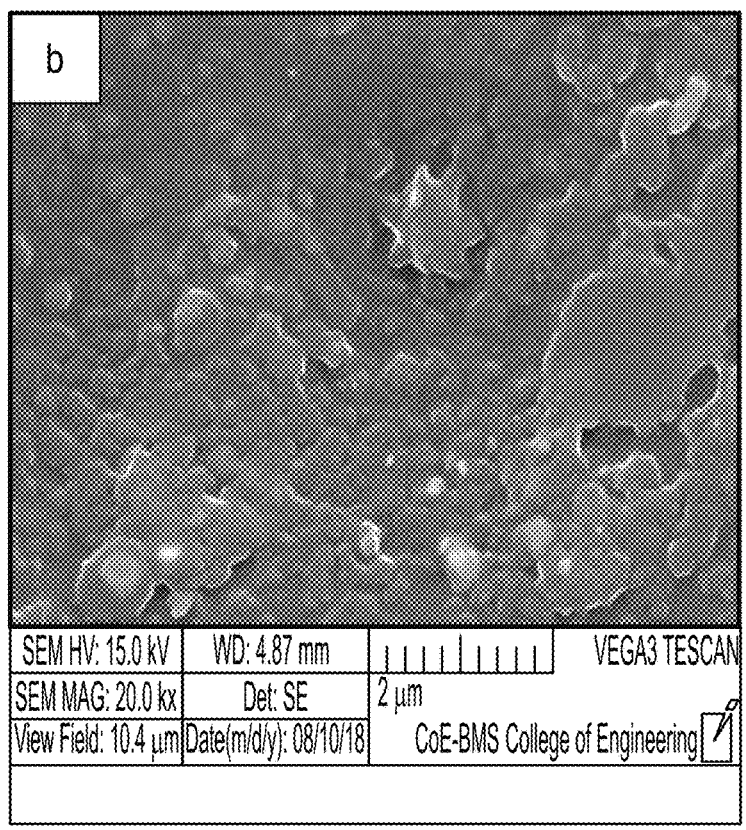

FIGS. 5A-5B show a typical SEM images of 1 wt % (FIG. 5A) and 5 wt % (FIG. 58) self-cured PMMA/h-BN nanocomposites formed under ultrasonic mixing. It is found that the nanoparticles are highly dispersed, and the texture is significant as we increase the amount of h-BN material into the composite.

Figure 6:
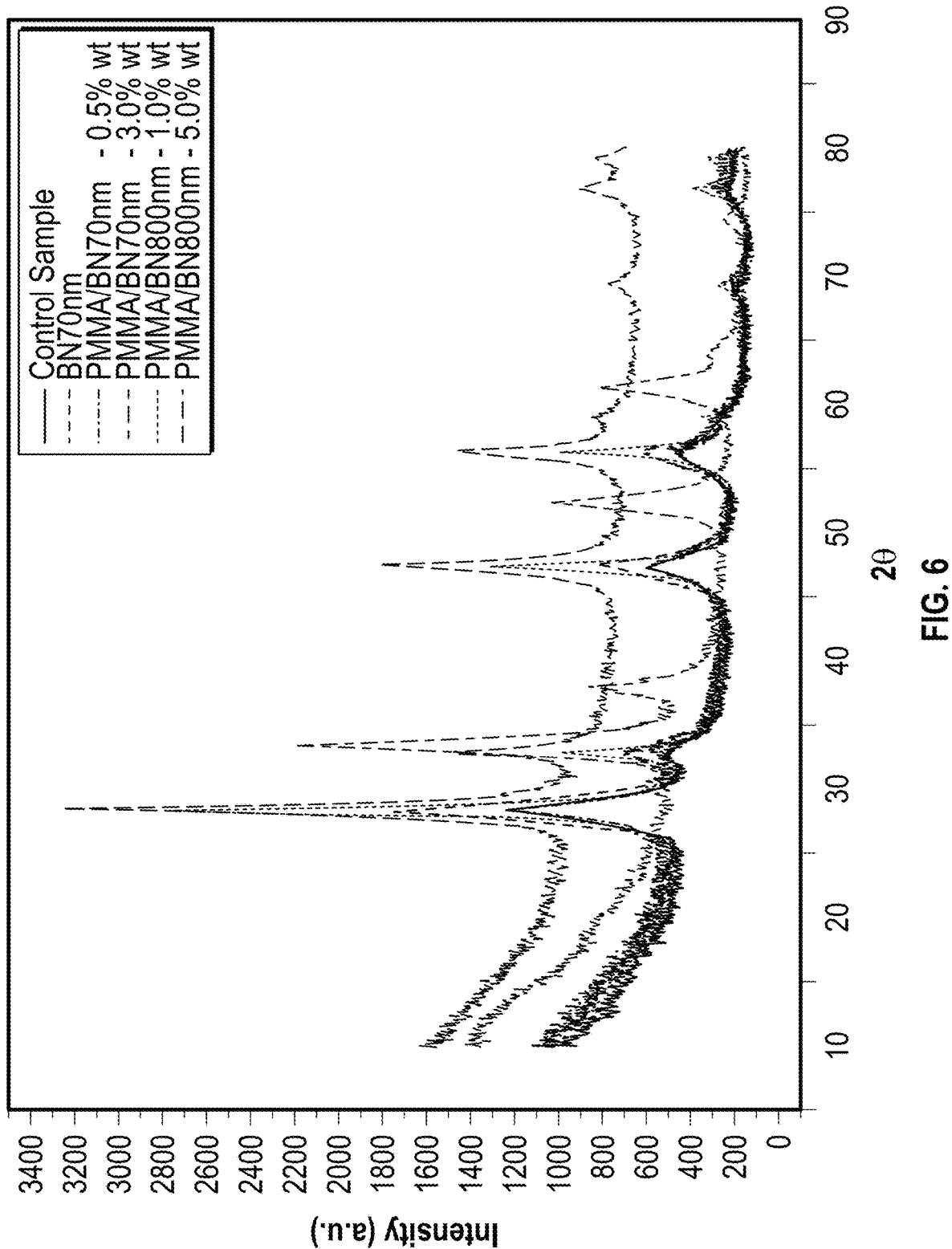
FIG. 6 is a graph showing the XRD patterns of the specimens of dental material made by ultrasonic mixing and which includes starting materials and nano-sized h-BN reinforcement with different concentrations, according to an embodiment of the present invention.

FIG. 6 shows the XRD patterns of the specimens made by ultrasonic mixing and which include starting materials and nano-sized h-BN reinforcement with different concentration. In the XRD observations, the four strongest peaks are detected at Bragg angles 27.5°, 33°, 47°, and 57° The peaks with Miller indices (002), (100), and (102) at 27.5°, 47°, and 57°, respectively, correspond to pure crystalline h-BN nanoparticle fillers. The control sample which represents bare PMMA has a semi-crystalline nature with a primary pick at 27.5°. It is observed that intensity of the peaks increases with the increase of h-BN concentration due to nanocomposite formation. This is true for 0.5 wt % versus 3.0 wt % for 70 nm h-BN fillers as well as 1.0 wt % versus 5.0 wt % for 800 nm h-BN fillers in PMMA. The peak corresponding to 1.0 wt % PMMA/BN800 shows higher intensity than the peak corresponding to 3.0 wt % PMMA/BN70 nm because of the large size of h-BN nanoparticles. Nevertheless, the characteristic peaks are higher in intensity which indicates that the nanocomposites are of good crystalline nature. No peaks corresponding to impurities are detected, showing that the final product is purely PMMA mixed with h-BN nano powder.

Figure 7:
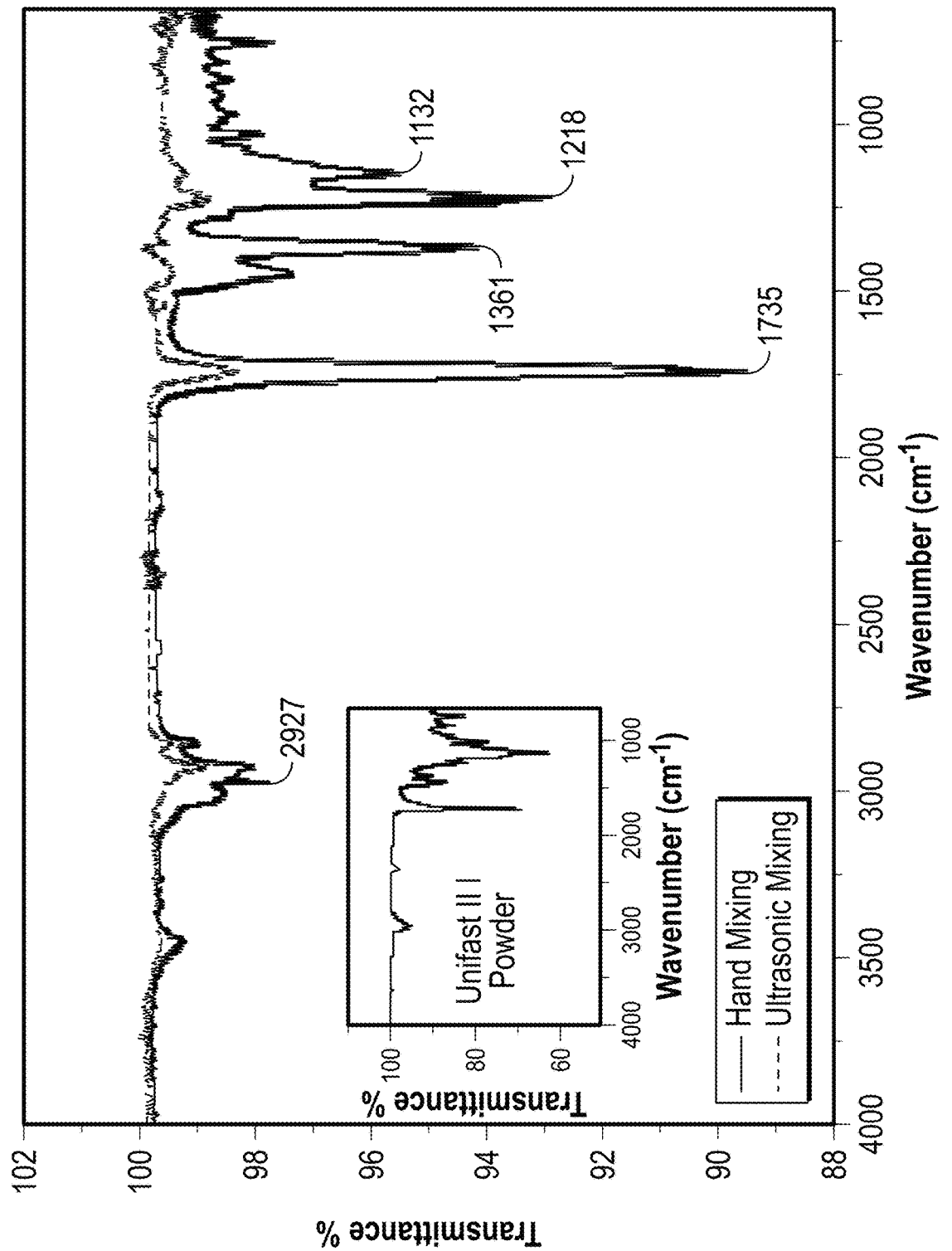
FIG. 7 is a graph showing FTIR data of dental material made by ultrasonic mixing for nano-sized h-BN reinforcement with different concentrations, according to an embodiment of the present invention.

FIG. 7 shows the FTIR spectrum of the control specimens made by both hand and ultrasonic mixing methods as well the spectrum corresponding to UNIFAST III powder. The band at around 1132 cm-1 is the characteristic absorption vibration of PMMA. The bands at about 1218 cm-1, 1361 cm-1, 1735 cm-1, and 2927 cm-1 are assigned to u(C—O) stretching vibration, wagging vibration of C—H, C=O stretching and C—H stretching, respectively. It is also found that specimens made by hand and ultrasonic mixing do not show similar FTIR spectrum. The spectrum of the specimen made by hand mixing is much like the one taken on pure UNIFAST III powder (FIG. 7 inset). This could be a sign that polymerization of the powder under liquid monomer is not fully complete as compared to specimen made by ultrasonic mixing.

Figure 8:
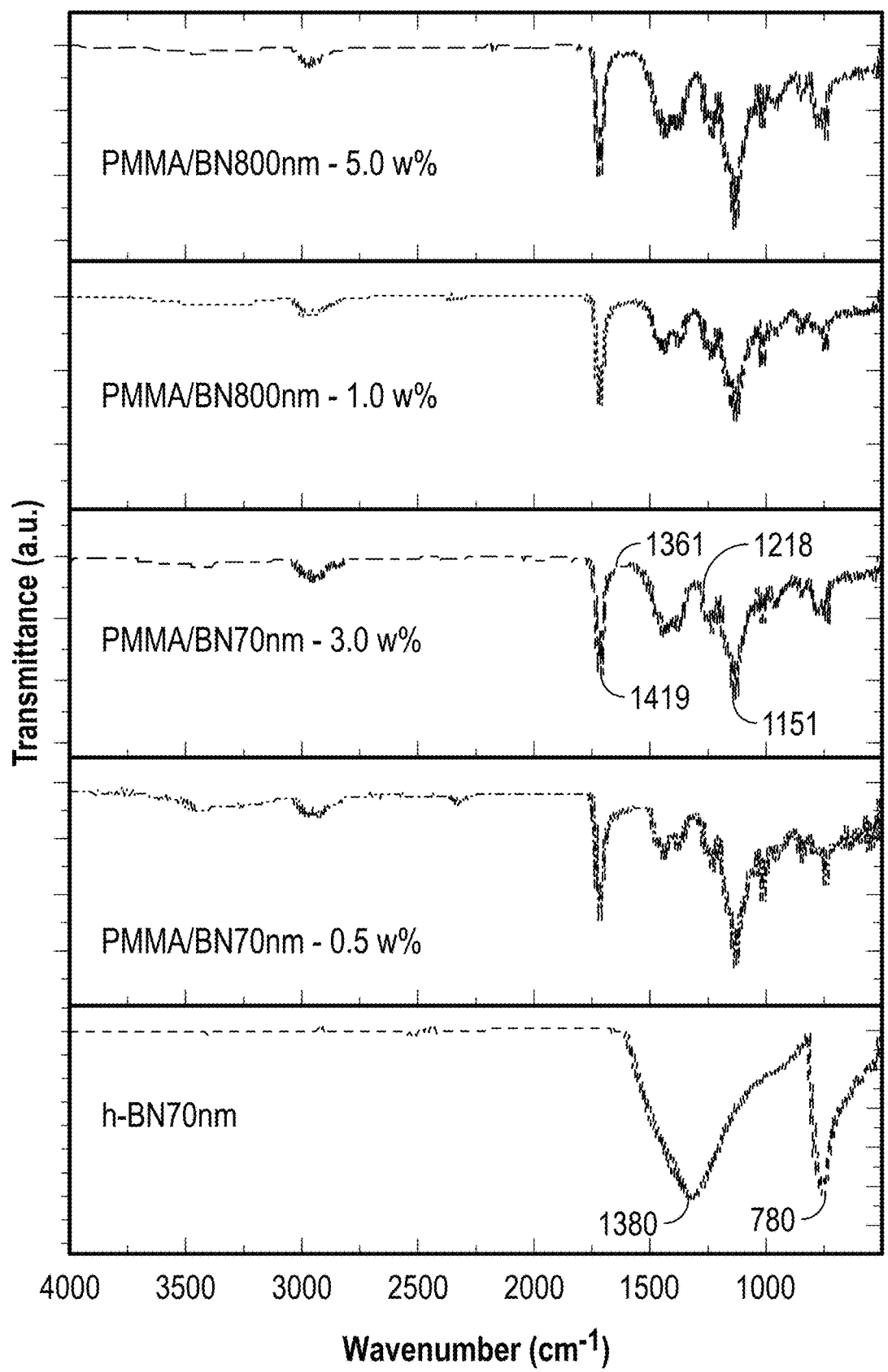
FIG. 8 is a series of graphs showing FTIR data of specimens of dental material made by ultrasonic mixing for nano-sized h-BN reinforcement with different concentrations, according to an embodiment of the present invention.
Figure 9:
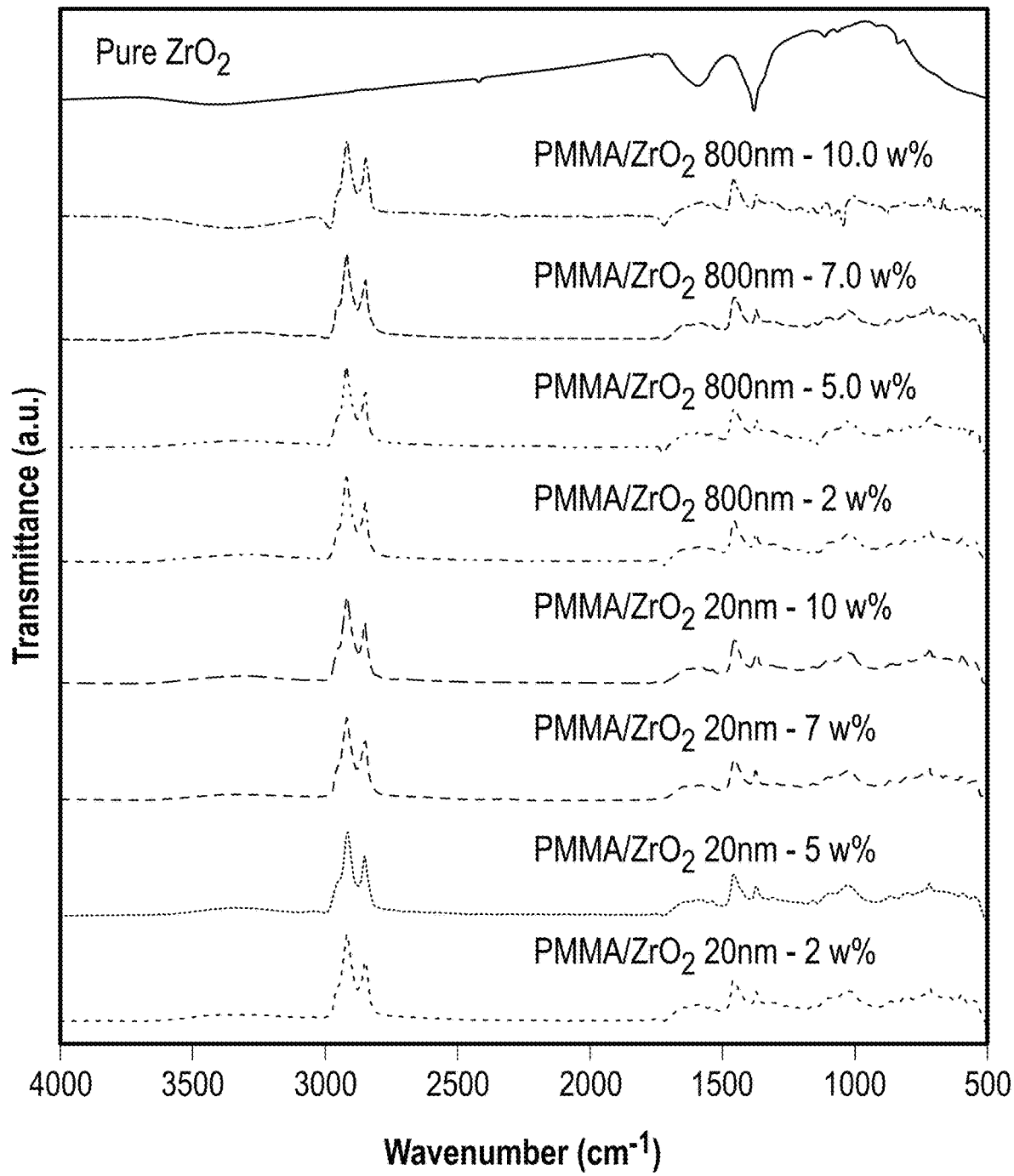
FIG. 9 is a series of graphs showing FTIR data of specimens of dental material made by ultrasonic mixing for nano-sized $ZrO_2$ reinforcement with different concentrations, according to an embodiment of the present invention.

FIG. 8 shows the FTIR data of the specimens made by ultrasonic mixing and which include starting materials and nano-sized h-BN reinforcement with different concentration. Several researchers have given IR data on variety of thin film BN, Most of investigators agree that there are two distinct IR absorption bands in boron nitride films. These are the band around 1380 cm·1 (in plane) and the band around 780 cm·1 (out of plane) which is due to B-N stretching and B-N-B bending, respectively. Entraining h-BN nano-powder into PMMA resulted in a modification of the molecular structure and therefore a change in the absorption spectrum. The local bands of the control samples at 1218 cm-1, 1361 cm-1 have shifted to 1151 cm-1, 1419 cm-1 as a result of PMMA interaction with the h-BN nanoparticles active mode at 1380 cm·1. The intensity is shown to increase with the increase of h-BN for a respective size, FIG. 9 shows the FTIR data of the specimens made by ultrasonic mixing and which include starting materials and $ZrO_2$ nanopowder reinforcement with different concentrations. The broad absorption band in the 3,396-1,760 $cm^{-1}$ range is due to the stretching vibrations of the water molecule OH groups, whereas the absorption band which appears at 1,600 $cm^{-1}$ is characteristic of the bending vibration of water molecules. It is uncertain whether the water observed in these spectra reflects the composition of the surface resulting from the heating process, or water which had rapidly attached to the surface during cooling. The peaks at 1,122 and 806 $cm^{-1}$ are due to the bending vibration of hydroxyl groups bound to zirconium oxide. Entraining $ZrO_2$ nano-powder into PMMA resulted in a modification of the molecular structure and therefore a change in the absorption spectrum. The local bands of the control samples at 1218 $cm^{-1}$, 1361 $cm^{-1}$ have shifted to 1028 $cm^{-1}$, 1459 $cm^{-1}$ as a result of PMMA interaction with the $ZrO_2$ nanoparticles active mode at 1376 $cm^{-1}$. The intensity is shown to increase with the increase of $ZrO_2$ for a respective size.

Figure 10:
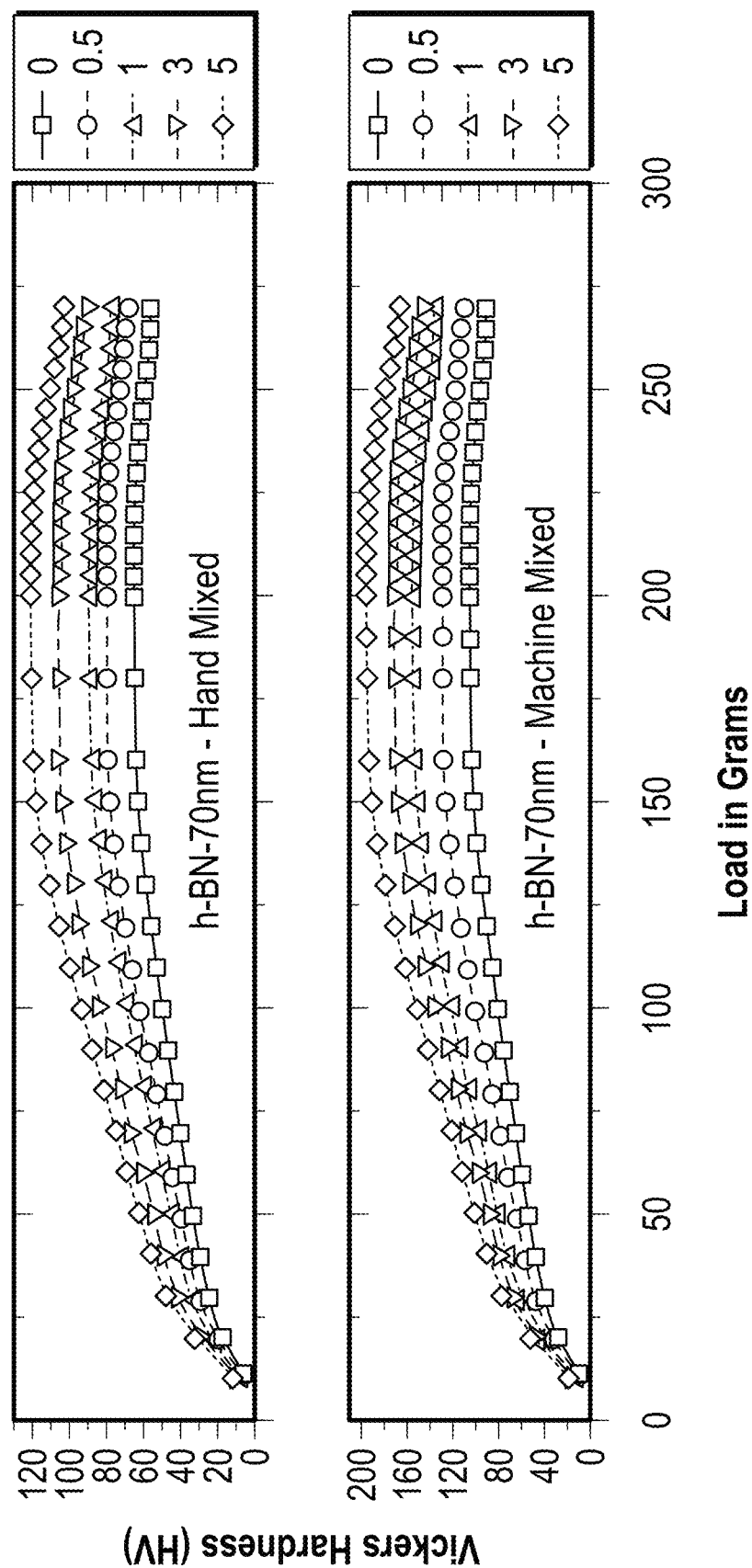
FIG. 10 is a series of graphs showing Vickers hardness (VH) measurements on specimens of dental material made by hand and ultrasonic mixing methods for 70 nm nano-sized h-BN reinforcement with different concentrations, according to an embodiment of the present invention.
Figure 11:
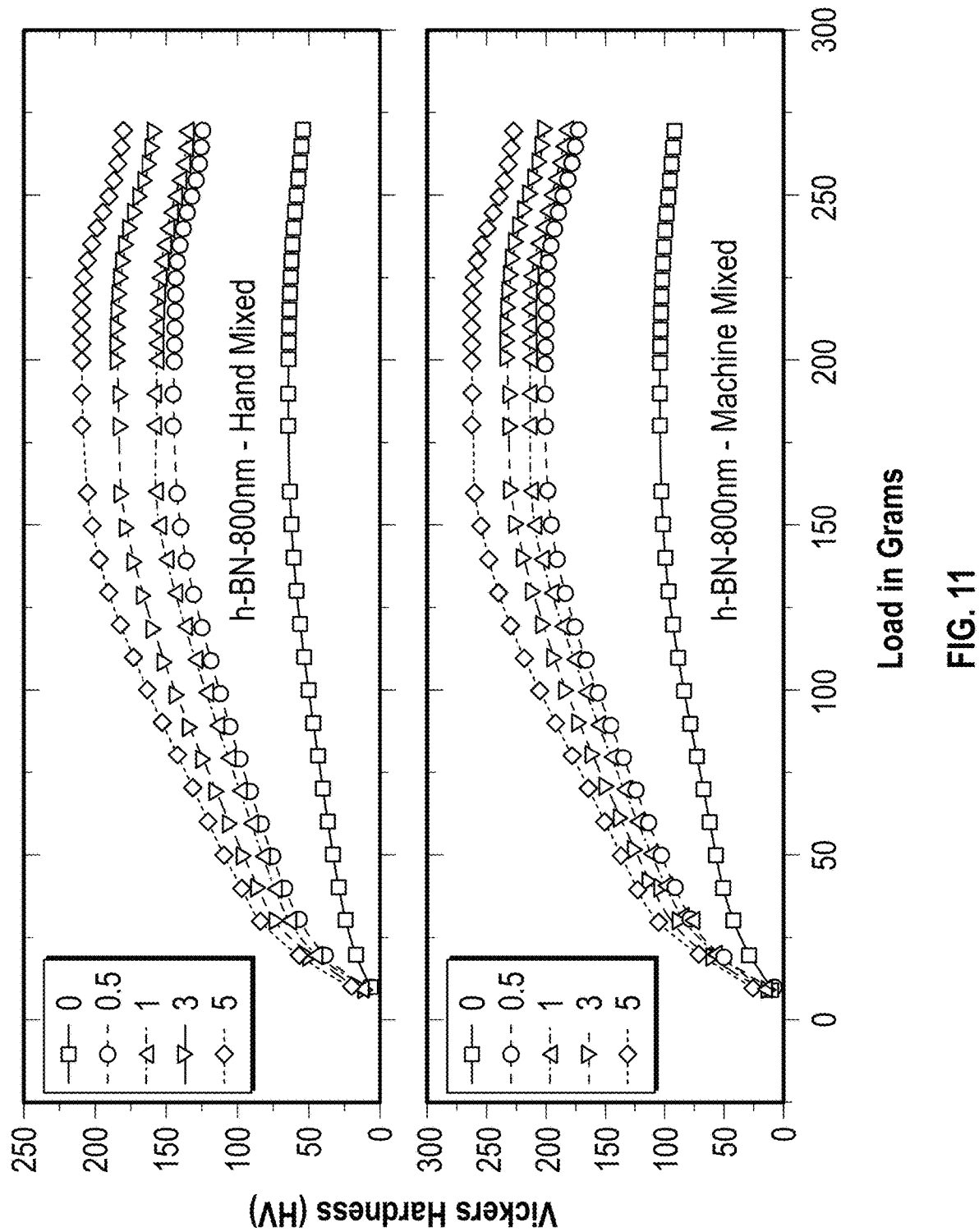
FIG. 11 is a series of graphs showing Vickers hardness (VH) measurements versus h-BN composition in PMMA on specimens of dental material made by hand and ultrasonic mixing methods for 800 nm nano-sized h-BN, according to an embodiment of the present invention.

FIGS. 10 and 11 show the Vickers hardness initially increased (VH) measurements on specimens made by hand and ultrasonic mixing methods and which include the control sample and nano-sized h-BN reinforced samples with different concentration. Initially, VH numbers increase with increasing load indicating the material resistance to plastic deformation. Then, VH stabilizes around a certain value (plateau region) at a load of 160 gf which defines the hardness value of the material beyond which the mechanical breakdown of the materials takes place at a load of 225 gf. The table below includes measured data on micro hardness, flexural strength, and bulk modulus carried on fabricated specimens. According to Material Property Database of pure PMMA, the hardness, flexural strength, and Young's modulus are within range.

Example 3

Dental material 100 was also made according to the methods described in the following Example 3, which describes additional methods and additional characteristics of the dental material 100 of an embodiment of the present invention.

Self-cured PMAA reinforced with h-BN and ZrO2 nanopowders were prepared by ultrasonic and hand blending techniques. The structural and mechanical properties of elaborated samples were characterized by using SEM, FTIR, micro indentation, bending strength, and modulus of elasticity techniques. The ultrasonic mixing method provided a fully complete polymerization process under liquid monomer as evidenced by FTIR measurements. Higher bending strengths and modulus of elasticity of the nanocomposite were recorded when using h-BN nanopowder fillers whereas hardness increased when using ZrO2 nanopowder. Overall, results showed that with respect to the unloaded samples made by manual mixing, blending a 5 wt % h-BN by ultrasonic mixing method increases the modulus of elasticity and the flexural strength values to 240% and 550%, respectively. However, a similar concentration of ZrO2 increased the Vickers Hardness values to 400%. This may suggest that PMMA loaded with an adjusted co-dispersion of h-BN and ZrO2 nanopowders in PMAA may lead to nanocomposites with high strength and high stiffness materials for making long-term dental inlays, crowns, bridges, and repairs. The resin GC UNIFAST III powder was mixed with GC UNIFAST liquid monomer to prepare the samples. The conventional liquid to powder ratio was 0.5 ml of liquid to 0.001 Kg of powder, however the liquid to powder ratio may vary between 0.001 L:0.002 Kg and 0.015 L:0.002 Kg. Both ultrasonic and hand blending procedures were performed in this investigation. The hand blending was completed in the same way it is usually performed at the dentist's office, where liquid solvent and powder are hand mixed together for less than 20 seconds. Depending on the type of sample, the blending of the nanocomposites was achieved by using an ultrasonic homogenizer at a power ranging from 20 Watts-225 Watts and the blending time varied between 10 seconds and 30 seconds. For both mixing methods, an exothermic reaction occurs during setting. When the blend becomes a soft dough, it was promptly filled into a tear-resistant 0.015 m diameter by 0.003 m thick disc mold made of Teflon. The two ends of the mold were opened (provided with holes). Compression molding was performed by pressing the samples against two flat glass plates, waiting for composite thermal setting, releasing the elaborated materials discs, and then taking off the extra material after each compression. For the boron nitride and zirconia strengthening fillers, h-BN nanopowders, 800 nm and 70 nm with a purity of 99.8% and stabilized zirconia ZrO2-8Y, 20 nm and zirconia ZrO2, 20 nm and 800 nm with a purity of 99.95% were purchased from US Research Nanomaterials, Inc.—USA. The proper loadings of BN and zirconia fillers for each mixture were measured using a micro gram Analytical Balance. When using BN as a filler, we prepared mixtures using 0.5, 1, 3, and 5% concentrations by weight (wt.) whereas for zirconia fillers, we prepared mixtures using 1, 2, 3, 5, 7, and 10% concentration by weight. Since nanopowders tend to agglomerate easily because of their high surface energy and available standard procedures cannot break-up their agglomerates, making well dispersed nanopowders in polymers is highly needed in achieving better mechanical properties.

The filler nanoparticles were first mixed with the UNIFAST liquid solvent and dispersed through sonication, then the obtained solution was poured into a small Pyrex beaker holding the UNIFAST III resin powder followed by an ultrasonic mixing.

We looked at the surface morphology images of the samples by using SEM TESCAN VEGA 3 LMU. Prior to taking the clear images and to avoid charging, a thin layer of gold was deposited on top of the samples. We recorded the FTIR (Perkin-Elmer series 600) response by using KBr disk method over a wavelength range from 400 cm-1 to 4000 cm-1. The Vickers hardness (Model: VH-5B) test technique was used to characterize the micro-hardness of the samples as per ASTM norm. The samples underwent first rough polishing and then fine polishing using a 3 microns grade paste. The hardness testing machine used a diamond indenter with a diameter of few microns. The indenter was made to strike the samples at different loading forces. In every recording, repeated strikes of the indenter are permitted for 20 seconds timing. The average diameters of the indentations of the samples were observed and recorded under the microscope attached to the Vickers hardness machine. Employing Formula 1, recorded VH values were multiplied by 9.807 so to read hardness in MPa. VH measurements were carried on for all unloaded (control) and loaded samples. The samples were cut out of the fabricated discs into bars with a diamond saw to allow measurements of the bending strength. The tooth is usually subjected to repeated chewing forces, both axial (compressive strength) and non-axial (flexural or bending strength) forces during the mastication process. The average compressive strength varies linearly with the average hardness. Both flexural strength and hardness are considered essential benchmarks for the tooth or dental repair stability and longevity under clinical loading conditions. Although we investigated flexural strength and not tensile strength, both describe the material's capacity in resisting deformation under loads, as the latter is more appropriate for ductile materials such as metals and it is also shape independent property. All bending bars (0.003 m length×0.025 m width) were polished with a 45 μm coarse diamond grinding wheel under running water followed with a two-step fine polishing by using 2.5 μm and 1 μm polycrystalline diamond pastes. We then carried repeated measurements for each of the polished bars. The number of bars for each test varies from 3 to 4 and the reported data represents the average values of recorded measurements for the tested samples. The flexural strength of the samples was carried out in three-point bending tests at a constant cross-head speed of 0.4 mm/min. The deflection and corresponding load were recorded.

The flexural strength was evaluated using Formula 2. The Young's modulus of the specimens was evaluated via a standard uniaxial state of stress testing method. Applying tension loads introduces stress in the object, thus increasing the initial length of the test sample. The rate of this expansion determines the modulus of elasticity also known as Young's modulus (E or Y). Young's modulus is commonly determined utilizing the Hooke's law for uniaxial stress which can be formulated as Formula 3.

Figure 12:
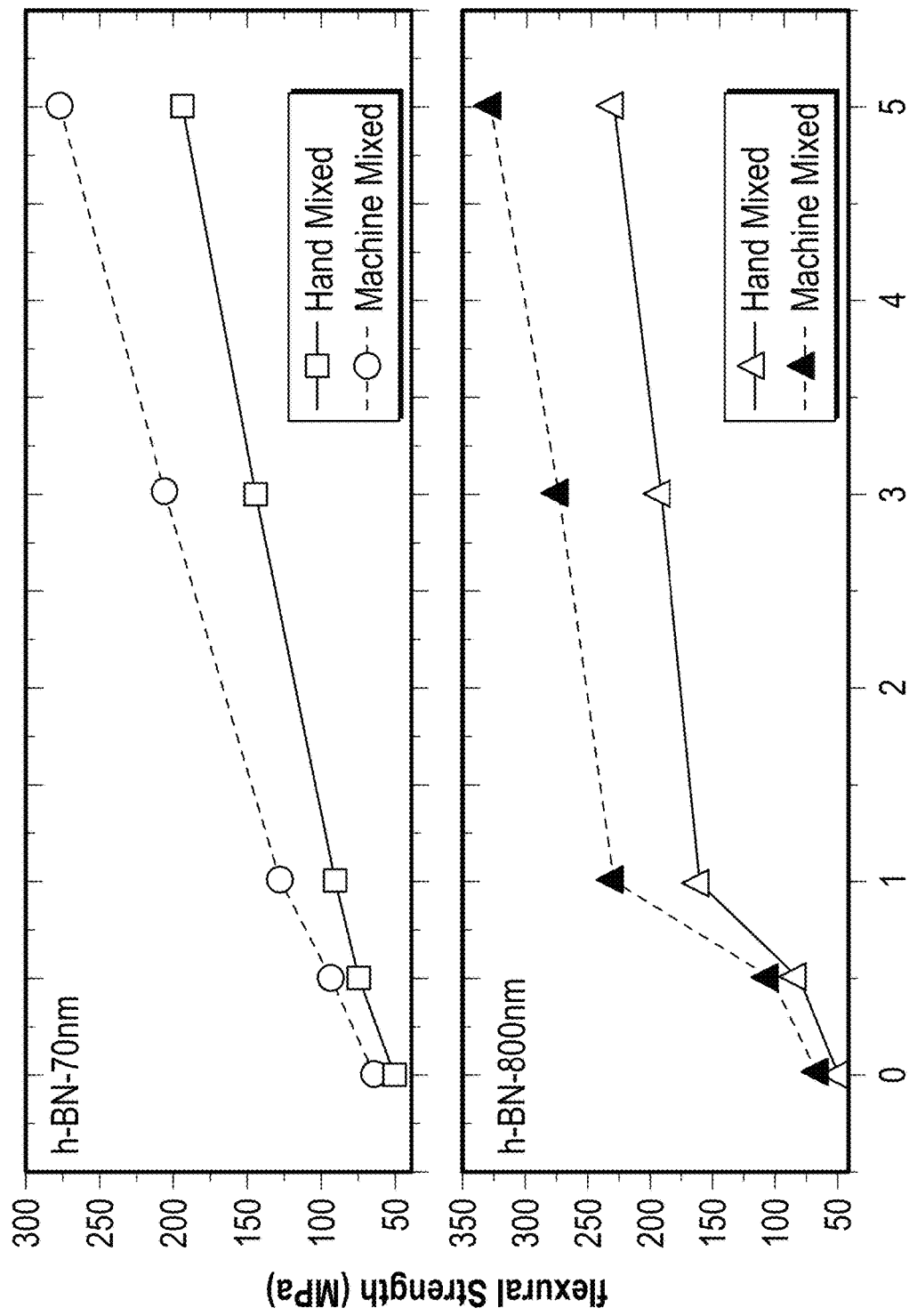
FIG. 12 is a series of graphs showing flexural strength measurements versus h-BN composition in PMMA on specimens of dental material made by hand and by ultrasonic mixing, according to an embodiment of the present invention.
Figure 13A:
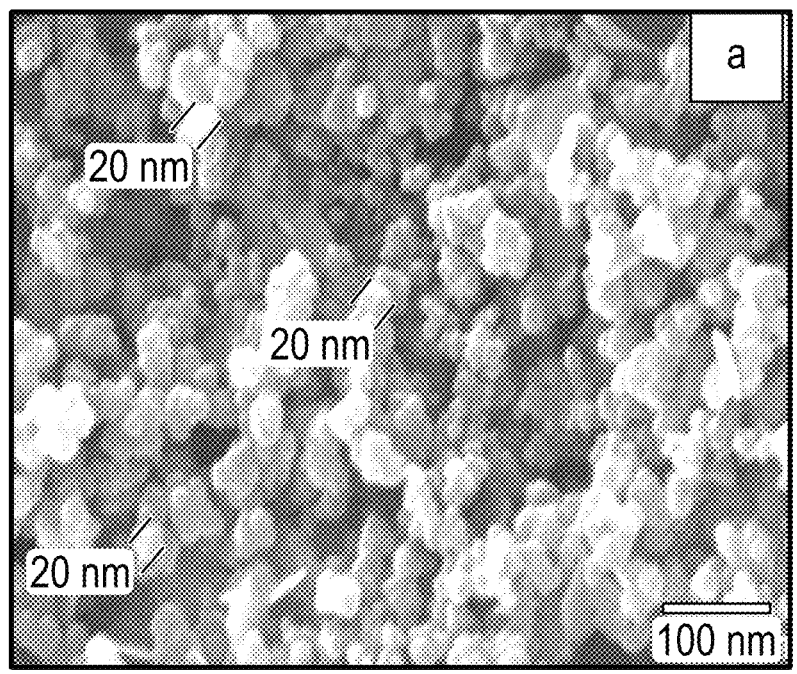
FIGS. 13A-13B are a series of SEM images of dental material comprising ZrO2-8Y nanopowder 20 nm reinforcement fillers which were used at similar concentration and its corresponding nanocomposite, according to an embodiment of the present invention.
Figure 13B:
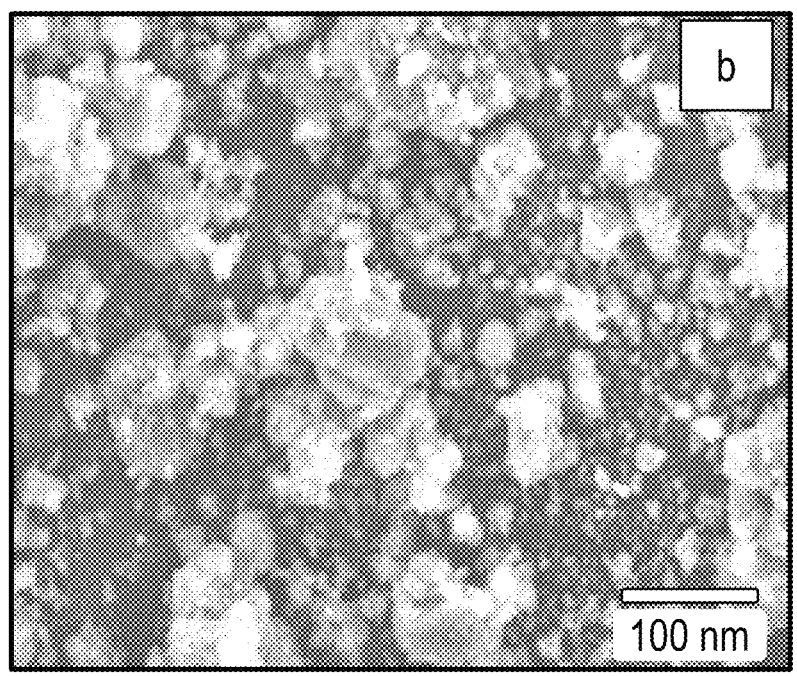

The provided scanning electron microscopy (SEM) images are for nanocomposites prepared by ultrasonic blending technique and reinforced with h-BN and zirconia nanofillers. FIGS. 12A-12B show SEM images of the h-BN 50-70 nm reinforcement filler and the corresponding nanocomposite at 0.5 wt %. FIGS. 13A-13B correspond to the SEM images of ZrO2-8Y nanopowder 20 nm reinforcement fillers which were used at similar concentration and its corresponding nanocomposite.

Figure 14:
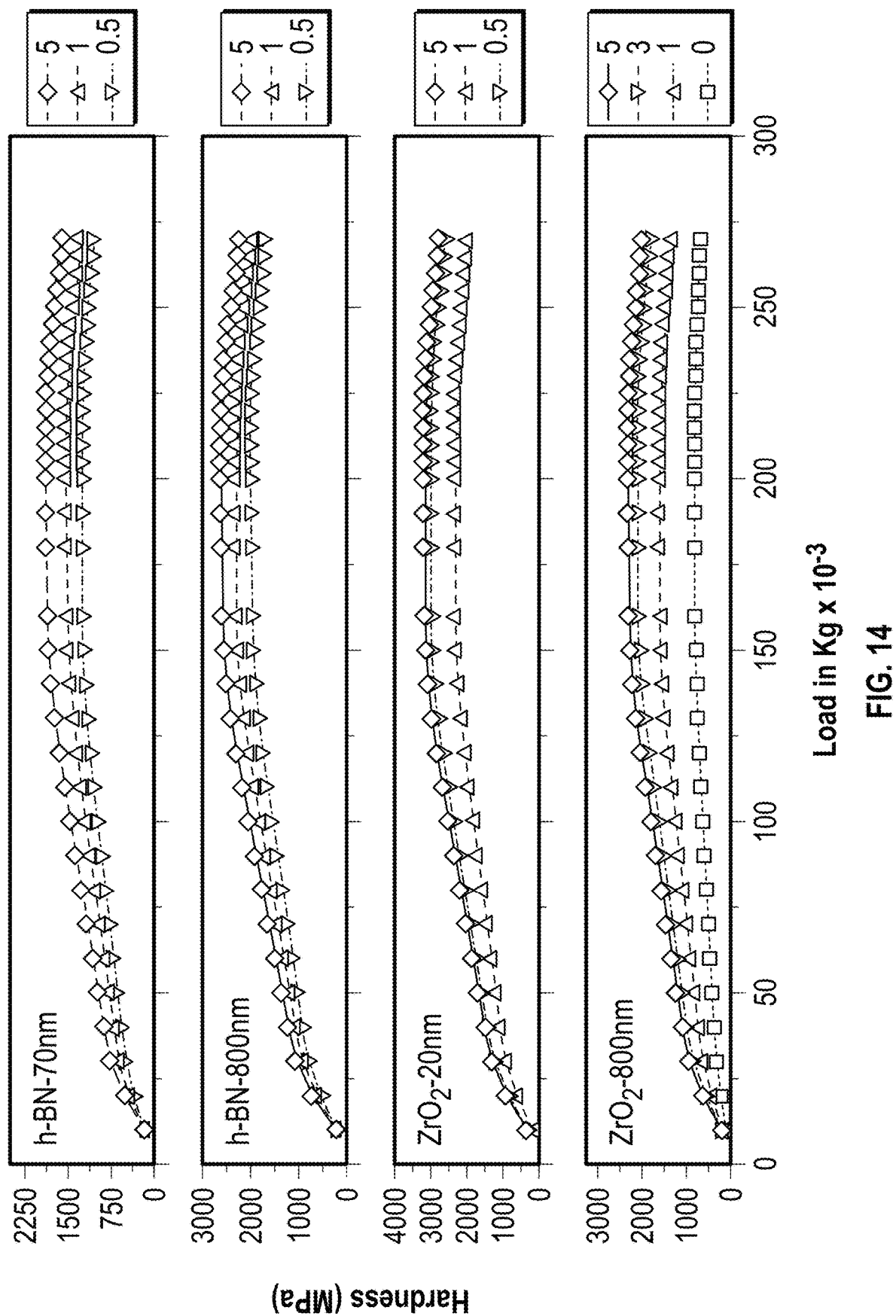
FIG. 14 is a series of graphs showing Vickers hardness (VH) measurements versus load on specimens of dental material made by ultrasonic mixing methods and reinforced with different concentrations of h-BN 70 nm and 800 nm and zirconia 20 nm and 800 nm, according to an embodiment of the present invention.

Table 1 (provided above in a previous example) includes the same measured data on micro hardness, flexural strength, and Young's modulus carried on fabricated specimens of the dental material of this example. Table 2 (provided below) includes some typical mechanical properties such as Young's modulus, flexural strength, hardness, Poisson's ratio, shear modulus, and material density for the bulk resin (PMMA), boron nitride, and zirconium oxide fillers. According to the cited references in Table 2 of pure PMMA, the hardness, flexural strength, and Young's modulus are within range. FIG. 14 shows the VH hardness measurements versus load on samples blended by ultrasonic mixing methods. This includes the unloaded sample and reinforced samples with h-BN nanopowder 70 nm and 800 nm and ZrO2-8Y nanopowder 20 nm and 800 nm powder nanofillers. As the load increases, the VH hardness initially increases as a result of the material showing resistance to change shape under elastic/plastic deformation. Then, hardness is maintained around a specific maximum value when the load reaches 0.160 Kgf after which the mechanical failure occurs at a load of 0.225 Kgf. The measured VH hardness values are 1019 MPa and 617 MPa for the control samples made by ultrasonic and hand blending, respectively. In term of hardness, it means that ultrasonic blending outperforms the manual one by an increment of over 65%.

TABLE 2

| | PMMA | h-BN | ZrO2 |
|---|---|---|---|
| Young Modulus | 2.76-3.30 GPa | 865 GPa | 200-210 GPa |
| Flexural Strength | 98-125 MPa | 70.5 GPa | 75 MPa |
| Hardness | 175 MPa | 46 GPa | 1.15 GPa |
| Poisson's ratio | 0.37 | −0.706 | 0.33 |
| Shear Modulus | 1.7 GPa | 1.12 GPa | 80 GPa |
| Density | 1.18 | 2.29 | 5.68 |

The VH hardness also increases when the loading of h-BN nanopowder increases in the pure PMMA samples. For samples made by ultrasonic blending, VH hardness reached values of 2569 MPa and 1863 MPa at 5 wt % of h-BN 800 nm h-BN 70 nm, respectively. In this case, we can state that with respect to pure PMMA made by hand mixing, the ultrasonic blending with h-BN nanofiller leads to about 300% increase in VH hardness.

When ZrO2-8Y was used as a filler, VH hardness reached a value of 3069 MPa when using 20 nm ZrO2-8Y at a loading of 5 wt %. This corresponded to an increase in VH hardness of about 200%. For samples made by hand blending, VH hardness reached a value of 2549 MPa versus 617 MPa when using same filler and same concentration. We can state that when using an ultrasonic mixing method combined with 20 nm in size and 5 wt % in weight of ZrO2-8Y powder, VH hardness increased to about 400% when compared to pure PMMA blended by hand mixing. The increase reached more than 600% when 10 wt % of the same filler is used.

Figure 15:
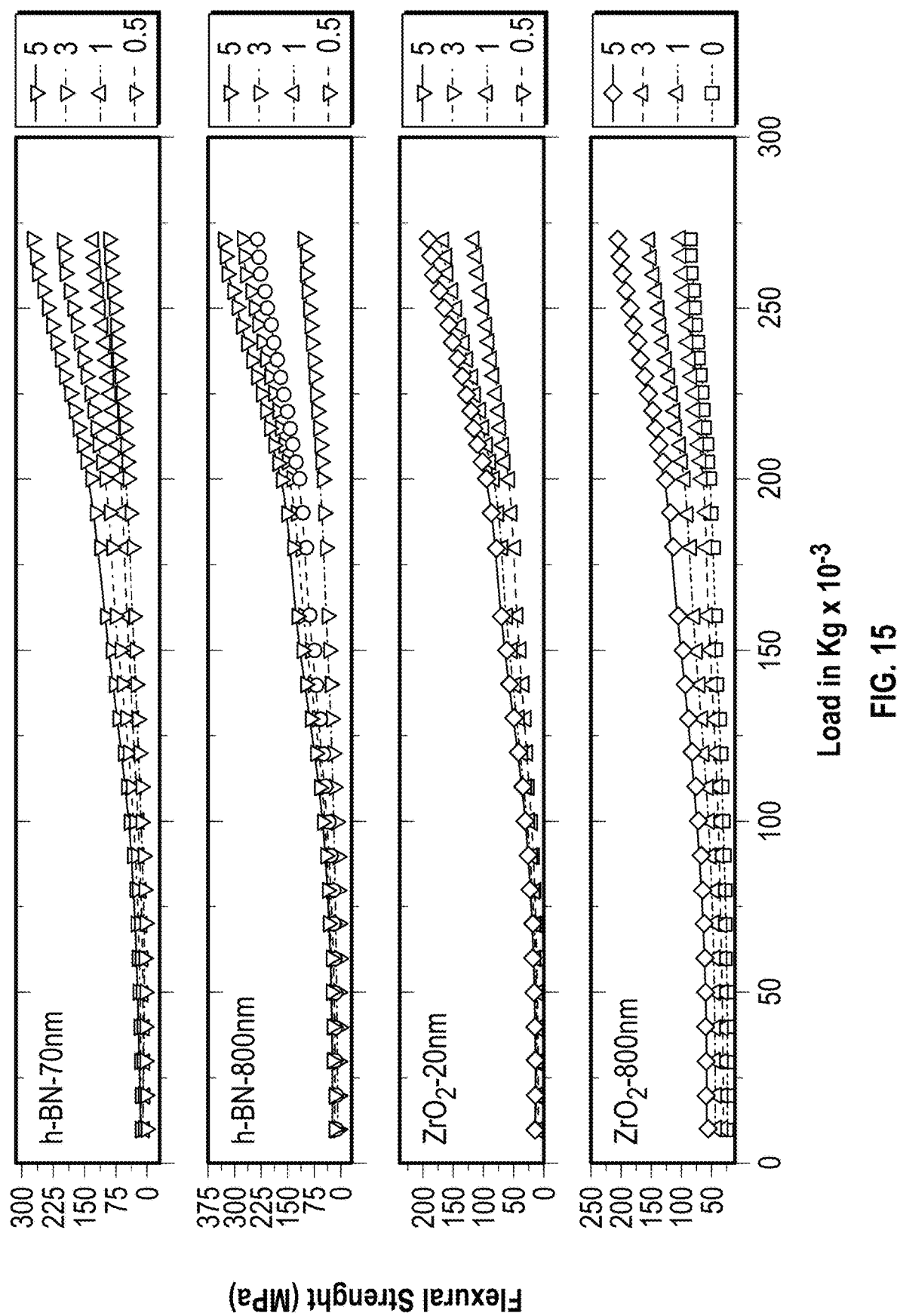
FIG. 15 is a series of graphs showing flexural strength (FS) measurements versus load on specimens of dental material made by ultrasonic mixing methods and reinforced with different concentrations of h-BN 70 nm and 800 nm and zirconia 20 nm and 800 nm, according to an embodiment of the present invention.

The flexural strength (FS) on samples made by ultrasonic blending versus load is presented on FIG. 15. This includes the control sample and reinforced samples with h-BN nanopowder 70 nm and 800 nm and ZrO2-8Y nanopowder 20 nm and 800 nm powder nanofillers. When load increases, FS initially increases as an indication of the material's level of rigidity. Measured stiffness strengths values were 65 MPa versus 50 MPa for control samples blended by hand and ultrasonic mixing methods, respectively. However, a 5 wt % loading of h-BN 800 nm brings FS to about 330 MPa. This corresponded to an increase in FS of more than 550%. When mixing a 1 wt % of BN nanotubes fraction in PMMA by using chemical vapor deposition method, the modulus of elasticity of the composite was increased up to 20% [37]. Better results in improving the mechanical properties were obtained when mixing BN nanoflakes and PMMA at a concentration of 2% per weight [38]. Here, both compressive strength and modulus of elasticity were increased by 150%.

When ZrO2-8Y was used as a filler and as the load increases, FS initially increases indicating the material degree of rigidity. FS is 190 MPa for specimen prepared by ultrasonic mixing of ZrO2-8Y 20 nm at a concentration of 5 wt %. With respect to hand mixing sample, this corresponded to an increase in FS of about 280% and reached about 800% at a concentration of 10 wt % of the same filler. When using ZrO2 800 nm similar concentration, FS reached a value of 206 MPa. This corresponded to an increase in FS of more than 300%. This increase can reach more than 450% at a concentration of 10 wt % of the same filler. In a more related work, zirconia was tried to enhance the fracture toughness material property of dental composites. Zirconomer is a commercial restorative dental brand that was developed by mixing the conventional glass ionomer cement (GIC) with a small portion of zirconia powder, so as to accomplish greater compressive and flexural strengths when compared with conventional Amalgam [39,40]. It has a significantly higher compressive strength as compared to GIC, 195 MPa versus 107 MPa. The diametrical tensile strength is also significantly higher for Zirconomer with 44.7 MPa compared to 17.6 MPa for GIC. This results in an increase of about 80% and 150% in compressive strength and tensile strength, respectively. In another reported work, zirconia nanoparticles were mixed with a bisphenol A-glycidyl methacrylate/Triethyleneglycol dimethacrylate dental composite. The highest flexural strength reached was about 118 MPa at 1% wt. of zirconia filler [41]. The result is much closer to our finding of 114 MPa when mixing 1% wt. of zirconia with UNIFAST III dental composite.

Figure 16:
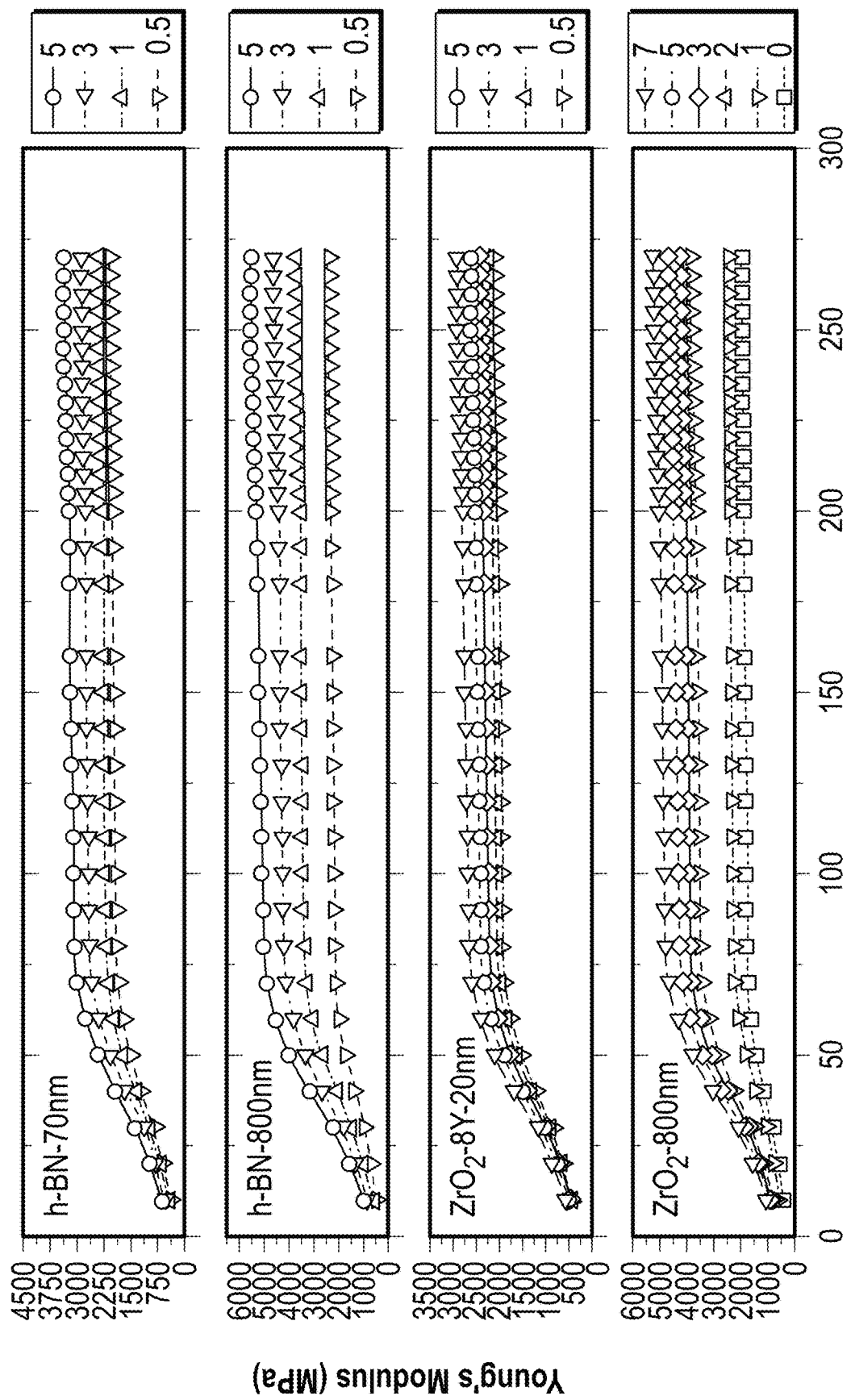
FIG. 16 is a series of graphs showing Young's modulus (YM) measurements versus load on specimens of dental material made by ultrasonic mixing methods and reinforced with different concentrations of h-BN 70 nm and 800 nm and zirconia 20 nm and 800 nm, according to an embodiment of the present invention.

FIG. 16 shows the Young's modulus (YM) measurements versus load on samples blended by ultrasonic mixing methods. This includes the pure PMMA and reinforced samples with h-BN nanopowder 70 nm and 800 nm and ZrO2-8Y nanopowder 20 nm and 800 nm powder nanofillers. When h-BN was used as a filler and as the load increases, the Young's modulus initially increases indicating the material ability to withstand compression and tension. Recorded Young's modulus values are 1758 MPa versus 1467 MPa for control samples blended by hand mixing. However, it reached 5032 MPa when using a loading of 5 wt % of h-BN 800 nm. This corresponded to an increase in YM of more than 240%. When using ZrO2 800 nm at the similar loading, FS reached a value of 206 MPa. This corresponded to an increase in FS of more than 300%. This increase can reach more than 450% at a concentration of 10 wt % of the same filler.

When ZrO2-8Y was used as a filler, the Young's modulus (YM) initially increased with increasing load indicating the material ability to withstand compression and tension. YM is 2381 MPa for specimen prepared by ultrasonic mixing of ZrO2-8Y 20 nm at a loading of 5 wt %. This corresponded to an increase in YM of more than 60% and it can reach more than 200% at a concentration of 10 wt % of the same filler. When using ZrO2 800 nm at the same loading, YM is 4241 MPa. This corresponded to an increase in YM of more than 180%. This increase reached more than 250% at a concentration of 10 wt % of the same filler.

Figure 17A:
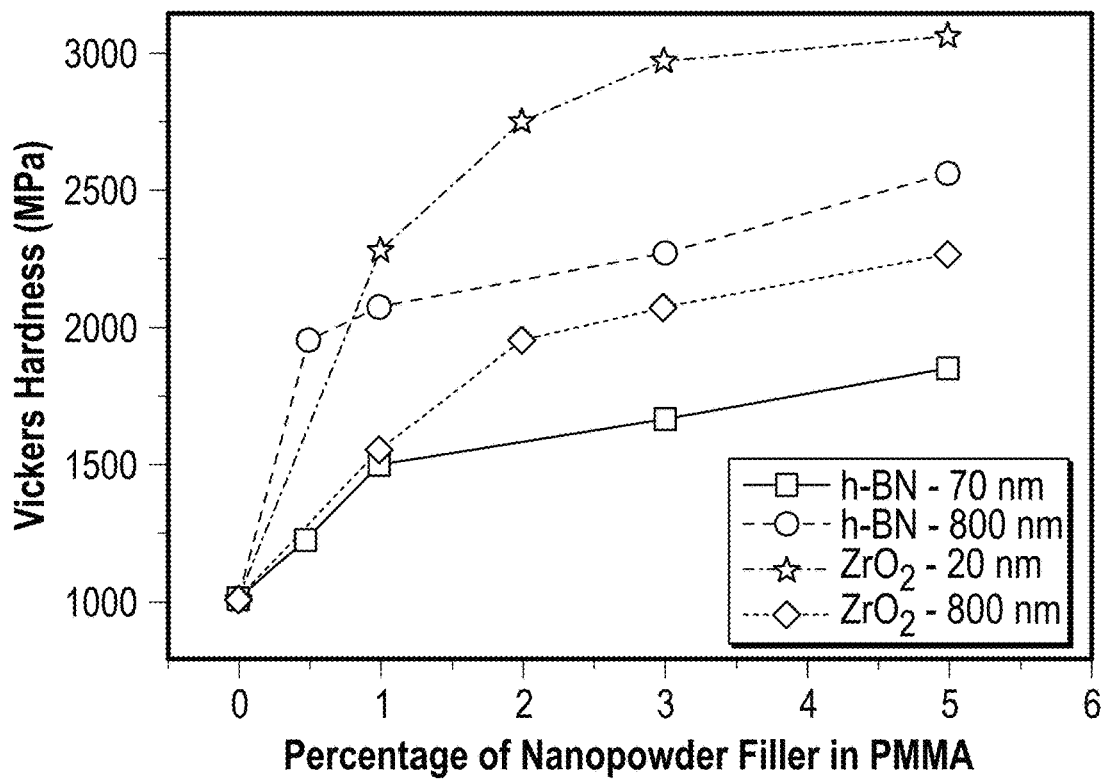
FIGS. 17A-17C are a series of graphs, FIG. 17A showing Vickers hardness, FIG. 17B showing flexural strength, and FIG. 17C showing Young's modulus measurement versus h-BN and zirconia compositions in PMMA on specimens of dental material made by the ultrasonic mixing method according to an embodiment of the present invention.
Figure 17B:
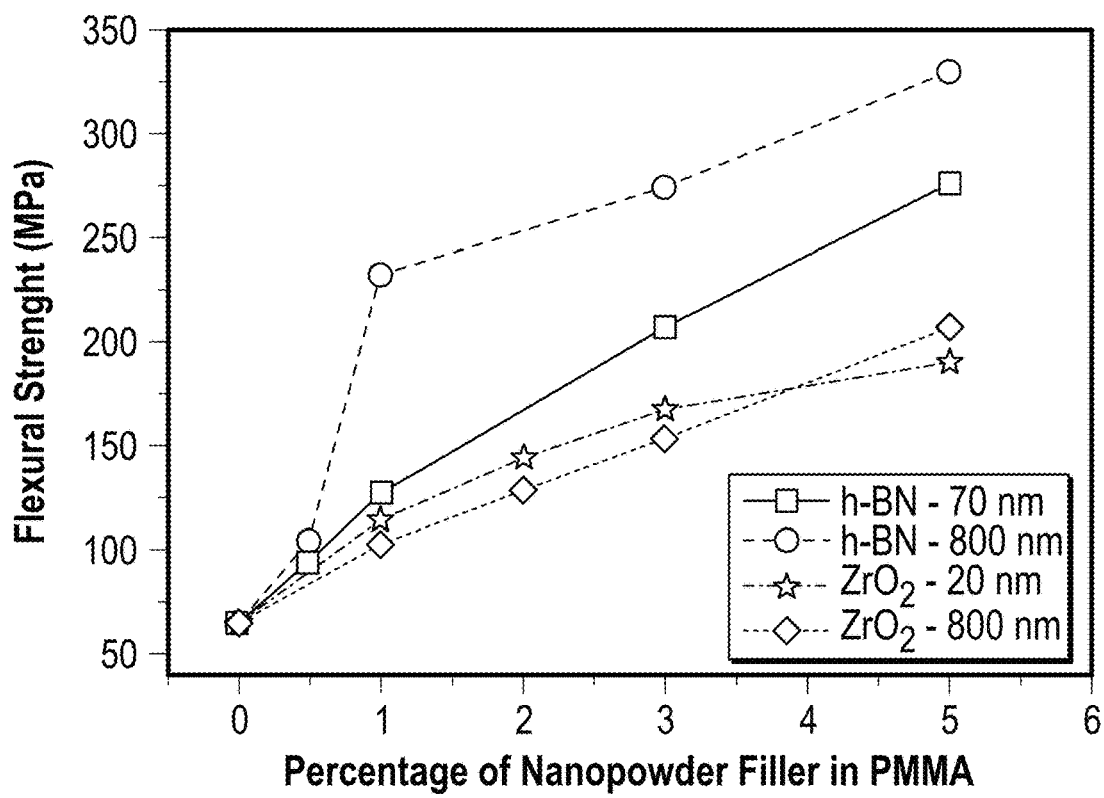
Figure 17C:
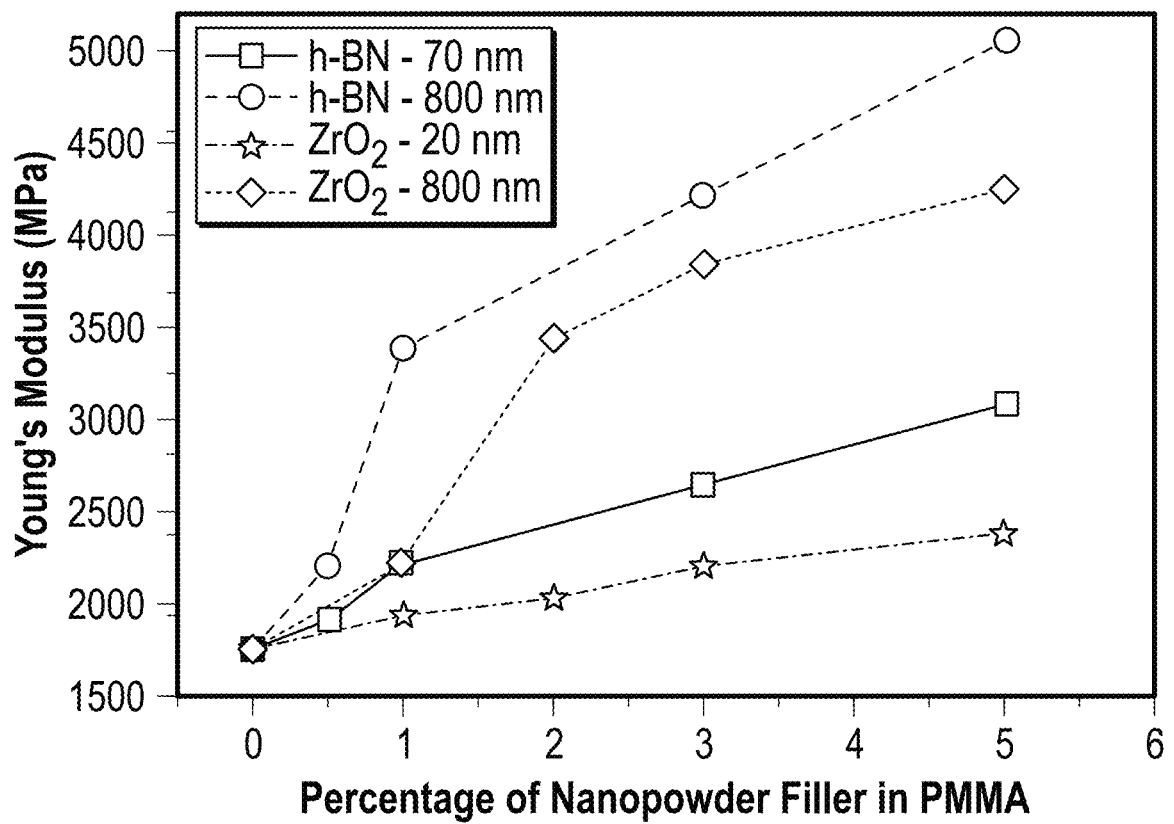

FIGS. 17A-C show the Vickers hardness, flexural strength, and Young's modulus measurement versus h-BN and zirconia compositions in PMMA on samples blended by the ultrasonic mixing method. Independently of the nanopowder used, the VH hardness, bending strength, and Young's modulus of the formed nanocomposites highly increase in values with the increase of the filler concentrations. In FIG. 17A, nanocomposites with ZrO2 nanopowder fillers show higher VH values than those with h-BN counterparts. The 8Y ZrQ2 20 nm are more effective than the ZrO2 800 nm with a relative enhancement in VH value of about 35% at a filler concentration of 5%. However, the h-BN 800 nm are about 40% more effective than h-BN 70 nm. FIG. 17B shows that nanocomposites with h-BN nanopowder fillers outperform their ZrO2 counterparts in term of FS values. Both h-BN 70 nm and 800 nm are more effective than the ZrO2 20 nm and 800 nm fillers with a relative increase in FS value of about 70% at a filler concentration of 5%. The nanocomposites formed with ZrO2 20 nm fillers are slightly higher in FS values for compositions up to 3%. We believe that as the amount of ZrO2 800 nm increases in the nanocomposites, the FS values become not conclusive. FIG. 17C shows a reciprocal behavior with Young's modulus as compared to VH hardness on FIG. 17A, The nanocomposites with h-BN nanopowder fillers show higher YM values than those with ZrO2 counterparts. The h-BN 800 nm are more effective than the h-BN 70 nm with a relative increase in YM value of about 65% at a filler concentration of 5%. The composites with ZrO2 800 nm are more effective than ZrO2 20 nm with a relative enhancement in YM value of about 80%. Overall, results showed that with respect to the unloaded samples made by manual mixing, blending a 5 wt % h-BN by ultrasonic mixing method increases the modulus of elasticity and the flexural strength values to 240% and 550%, respectively. However, a similar concentration of 8Y ZrO2 increases the Vickers Hardness numbers (VH) to 400%. So, on one hand h-BN increases both the bending strength and the modulus of elasticity values of the nanocomposite and on the other hand, ZrO2 increases the hardness of the nanocomposite. Therefore, if we make a controllable co-dispersion of h-BN and ZrO2, it may be possible to synthesize nanocomposites with higher performance with respect to both hardness and bending strength combined. This may suggest that PMMA loaded with a combination of h-BN and ZrO2 nanopowders may lead to nanocomposites with high strength high stiffness materials for making long-term dental inlays, crowns, bridges, and repairs. We have attempted to predict the elastic properties of the nanocomposites by looking into micromechanics models. These models appear to sufficiently predict the elastic moduli for 1 D (nanorods, nanowires, needle-like) as well as for 2D nanocomposites such as fiber or clay reinforced composites where the aspect ratio of the filler plays a significant role. The stiffening of these mechanical structures gets higher due to large aspect ratios of the fiber but unfortunately it is also proportional to the degree of porosity that comes with it. Furthermore, one must assume the elastic properties and density of the nanoparticles are equal to their respective bulks. Nevertheless, these fibrous fillers may find applications in dental adhesive layers to improve the bond strength. However, for restorative dental or repair material, the porosity should be reduced if not suppressed to meet many conditions for clinical oral health. The rule of mixture may also apply well for fiber-reinforced composites, assuming that all the fibers are aligned in one direction. In the case of isostrain condition (force parallel to fiber direction), it gives stiff and strong composite whereas in the case of isostress condition (force perpendicular to fiber direction) it gives soft and weak composite. In our case, we have nanoparticles with zero dimension, and the values of expected elastic properties of the nanocomposite would be somewhere in between the two extremes but close to the polymer side. Factors such as concentration, quality of dispersion, size, shape, and surface treatment of nanoparticles can affect the reinforcement properties of the nanocomposites. Furthermore, same nanoparticles with different concentrations can lead to optimum mechanical strength when entrained in various polymers. It is not uncommon for a low concentration of fillers to give maximum values for the mechanical properties in polymers while further increase in concentration results in degradation of such properties.

The following reported works on other reinforcements for non-dental purposes which were used as polymer scaffolds in bone repairs, provide useful information that may explain the reinforcing mechanism of h-BN and ZrO2 nanopowders on the hardness, flexural strength, and Young's modulus of PMMA. In order to improve the mechanical properties of poly-L-lactic acid (PLLA) which is a potential material used in bone repair, a typical zeolitic imidazolate framework (ZIF-8) was introduced by a selective laser sintering technique into PLLA scaffolds. Results show that both compressive and tensile strengths were improved by 85.6% and 36.9%, respectively. Such improvement was attributed to the tight interface bonding of PLLA matrix with the active nucleation sites of ZIF-8 nanoparticles which is believed due to their hydrophobicity characters. While PMMA and zirconia are considered hydrophilic, h-BN is mostly hydrophobic with a partial hydrophilic character. This may explain why the hardness significantly increases when using zirconia fillers at 5 wt % while an equal concentration of h-BN increases the flexural strength and the modulus of elasticity of the nanocomposites. The partial hydrophilicity character of h-BN is believed to generate less tight chemical bonds with the surrounding molecular chains of PMMA which gives some degree of movement and flexibility.

The design of new materials would overcome the brittle nature of composites used in dental repairs for instance. To that end, crack propagation at the interfaces PMMA/h-BN and PMMA/ZrO2 needs to be investigated. According to a reported work on layered clay/epoxy composites, the fracture properties of such polymer nanocomposites with interphase (IP) zones can be predicted using a phase field approach to model the matrix and the IP zone. The model also allows to extract the dissipation or fracture energy rates due to fractures for different thicknesses of the corresponding IP zones. The fracture energy which indicates the nanocomposite resistance to crack growth was investigated by using a stochastic modelling involving IP zones in epoxy nanocomposites. The model was constructed followed by a sensitivity analysis (SA) which accounts for uncertainties in the input parameters. The maximum possible stress and modulus of elasticity were found to be the most influential inputs on the fracture variance. This type of modeling based on SA is very costly and a SA toolbox consisting of a set of Matlab can be used for computationally expensive models. Another strategy that is significantly challenging would be to use a multiscale modeling of fractures. This method is extensive but powerful for extracting material properties based on atomistic scale details. An open-source tool called PERMIX was carried on successfully to handle fractures using multiscale modeling of cracks in particular.

The preceding examples can be repeated with similar success by substituting the generically or specifically described components and/or operating conditions of embodiments of the present invention for those used in the preceding examples.

Note that in the specification and claims, "about" or "approximately" means within twenty percent (20%) of the numerical amount cited. For removal of doubt, it should be understood that any range stated in this written description that does not specifically recite the term "about" before the range or before any value within the stated range inherently includes such term to encompass the approximation within the deviation noted above. As used herein, the words "a", "an" or "the" refers to one or more unless otherwise indicated.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

What is claimed is:

1. A method of preparing a dental material comprising:
creating a solvent-filler mixture by ultrasonically mixing at least one filler with a liquid monomer solvent, wherein the at least one filler comprises boron nitride, wherein the boron nitride comprises boron nitride in wurtzite form; and
subsequently mixing the solvent-filler mixture with a powder resin to create a composite, wherein the ratio of resin to solvent-filler mixture is between about 2.0 gm of powder resin to about 1.0 ml of solvent-filler mixture and about 2.0 gm of powder resin to about 2.0 ml of solvent-filler mixture.

2. The method of claim 1, further comprising pouring the composite into a mold.

3. The method of claim 2 wherein the mold comprises an opening to release extra composite, and further comprising pressing the mold with the composite therein by compression.

4. The method of claim 2, further comprising pressing the mold with the composite therein by compression and setting the mold with the compressed composite therein to form the dental material.

5. The method of claim 4, further comprising milling the dental material to form a dental restoration.

6. The method of claim 1, wherein the boron nitride comprises boron nitride in hexagonal form (h-BN).

7. The method of claim 6, wherein the dental material comprises a concentration of between about 0.25% and 10% by weight of h-BN.

8. The method of claim 1, wherein the boron nitride has an average particle size of about 10 nm to about 800 nm.

9. The method of claim 1, wherein the at least one filler further comprises zirconia and the dental material comprises a concentration of between about 0.5% and about 20% by weight of zirconia.

10. The method of claim 9, wherein the zirconia has an average particle size of about 20 nm to about 800 nm.

11. The method of claim 1, wherein the resin is a self-curing acrylic resin comprising ethyl-methyl methacrylate polymer and polymethylmethacrylate.

12. The method of claim 1, wherein the solvent is a liquid monomer comprising: methyl methacrylate; ethyleneglycol dimethacrylate; and trimethylolpropane trimethacrylate.

13. The method of claim 1, wherein
the powder resin comprises ethyl-methyl methacrylate polymer at a concentration greater than about 70% and polymethylmethacrylate at a concentration less than about 30%;
the liquid solvent comprises about 92.0% Methyl methacrylate, about 4.0% N,N-dimethyl-p-toluidine, about 2.0% Ethyleneglycol dimethacrylate and about 1.8% Trimethylolpropane trimethacrylate; and
the at least one filler comprises boron nitride and zirconia, wherein the boron nitride is in hexagonal form with particles having an average particle size of between about 10 nm and about 800 nm and making up between about 0.25% and about 10% by weight of the dental material, and wherein the zirconia has an average particle size of between about 20 nm and about 800 nm and making up between about 0.5% and about 20% by weight of the dental material; and further comprising:

pouring the composite into a mold;

pressing the mold with the composite therein by compression, wherein the mold comprises an opening to release extra composite from the mold; and setting the mold with the compressed composite therein to form the dental material.

14. The method of claim 13 further comprising milling the dental material to form a dental restoration.

15. A method of preparing a dental material comprising:

creating a solvent-filler mixture by ultrasonically mixing at least one filler with a liquid monomer solvent, wherein the at least one filler comprises boron nitride, wherein the boron nitride comprises boron nitride in amorphous form; and subsequently mixing the solvent-filler mixture with a powder resin to create a composite, wherein the ratio of resin to solvent-filler mixture is between about 2.0 gm of powder resin to about 1.0 ml of solvent-filler mixture and about 2.0 gm of powder resin to about 2.0 ml of solvent-filler mixture.

16. The method of claim 15, further comprising pouring the composite into a mold.

17. The method of claim 16 wherein the mold comprises an opening to release extra composite, and further comprising pressing the mold with the composite therein by compression.

18. The method of claim 16, further comprising pressing the mold with the composite therein by compression and setting the mold with the compressed composite therein to form the dental material.

19. The method of claim 18, further comprising milling the dental material to form a dental restoration.

20. The method of claim 15, wherein the at least one filler further comprises zirconia and the dental material comprises a concentration of between about 0.5% and about 20% by weight of zirconia.

* * * * *